United States Patent
Yu et al.

(10) Patent No.: US 11,191,511 B2
(45) Date of Patent: Dec. 7, 2021

(54) METHOD AND APPARATUS FOR IMAGE RECONSTRUCTION AND CORRECTION USING INTER-FRACTIONAL INFORMATION

(71) Applicant: Accuray, Inc., Sunnyvale, CA (US)

(72) Inventors: Zhicong Yu, Highland Hts., OH (US); Chuanyong Bai, Solon, OH (US); Amit Jain, Solon, OH (US); Daniel Gagnon, Twinsburg, OH (US); Jacob Shea, Madison, WI (US); Wenli Wang, Briarcliff Manor, NY (US); Calvin R. Maurer, Jr., San Jose, CA (US)

(73) Assignee: Accuray, Inc., Sunnyvale, CA (US)

( * ) Notice: Subject to any disclaimer, the term of this patent is extended or adjusted under 35 U.S.C. 154(b) by 18 days.

(21) Appl. No.: 16/694,230

(22) Filed: Nov. 25, 2019

(65) Prior Publication Data
US 2020/0170607 A1  Jun. 4, 2020

Related U.S. Application Data

(60) Provisional application No. 62/773,712, filed on Nov. 30, 2018, provisional application No. 62/773,700, (Continued)

(51) Int. Cl.
*A61B 6/00* (2006.01)
*G06T 11/00* (2006.01)
(Continued)

(52) U.S. Cl.
CPC ............ *A61B 6/5282* (2013.01); *A61B 6/027* (2013.01); *A61B 6/032* (2013.01); *A61B 6/06* (2013.01);
(Continued)

(58) Field of Classification Search
CPC .... A61N 5/1067; A61N 5/107; A61N 5/1071; A61N 5/1082; A61N 2005/1085;
(Continued)

(56) References Cited

U.S. PATENT DOCUMENTS

| | | | |
|---|---|---|---|
| 4,190,773 A | 2/1980 | Braden et al. | |
| 5,615,279 A | 3/1997 | Yoshioka et al. | |

(Continued)

FOREIGN PATENT DOCUMENTS

| | | |
|---|---|---|
| DE | 10 2006 007058 A1 | 7/2007 |
| EP | 1062914 A1 | 12/2000 |

(Continued)

OTHER PUBLICATIONS

International Search Report and Written Opinion from PCT/US2019/063080 dated Mar. 16, 2020.

(Continued)

*Primary Examiner* — Courtney D Thomas
(74) *Attorney, Agent, or Firm* — Calfee, Halter & Griswold LLP

(57) ABSTRACT

An imaging apparatus and associated methods are provided to efficiently estimate scatter during multi-fraction treatments for improved quality and workflow. Estimated scatter from one fraction during a treatment course can be utilized during subsequent fractions, allowing for measurements with higher scatter-to-primary ratios. The quality of scatter estimates can be maintained, while workflow improves and dosage decreases. Scan configuration limits can be utilized to maintain a minimum level of scatter measurement quality. Patient information can be monitored to ensure that prior fraction scatter estimates are still applicable to current patient status.

20 Claims, 10 Drawing Sheets

Related U.S. Application Data filed on Nov. 30, 2018, provisional application No. 62/796,831, filed on Jan. 25, 2019, provisional application No. 62/800,287, filed on Feb. 1, 2019, provisional application No. 62/801,260, filed on Feb. 5, 2019, provisional application No. 62/813,335, filed on Mar. 4, 2019, provisional application No. 62/821,116, filed on Mar. 20, 2019, provisional application No. 62/836,357, filed on Apr. 19, 2019, provisional application No. 62/836,352, filed on Apr. 19, 2019, provisional application No. 62/843,796, filed on May 6, 2019, provisional application No. 62/878,364, filed on Jul. 25, 2019.

(51) Int. Cl.

| | | |
|---|---|---|
| *A61B 6/03* | (2006.01) | |
| *A61B 6/06* | (2006.01) | |
| *A61B 6/02* | (2006.01) | |
| *A61N 5/10* | (2006.01) | |
| *A61B 6/08* | (2006.01) | |
| *G06T 7/30* | (2017.01) | |
| *A61B 5/055* | (2006.01) | |
| *A61B 6/04* | (2006.01) | |

(52) U.S. Cl.
CPC ............ *A61B 6/405* (2013.01); *A61B 6/4078* (2013.01); *A61B 6/4085* (2013.01); *A61B 6/469* (2013.01); *A61B 6/488* (2013.01); *A61B 6/5205* (2013.01); *G06T 11/005* (2013.01); *A61B 5/055* (2013.01); *A61B 6/025* (2013.01); *A61B 6/03* (2013.01); *A61B 6/035* (2013.01); *A61B 6/0407* (2013.01); *A61B 6/08* (2013.01); *A61B 6/4014* (2013.01); *A61B 6/4021* (2013.01); *A61B 6/4028* (2013.01); *A61B 6/4064* (2013.01); *A61B 6/4435* (2013.01); *A61B 6/4441* (2013.01); *A61B 6/4458* (2013.01); *A61B 6/481* (2013.01); *A61B 6/482* (2013.01); *A61B 6/483* (2013.01); *A61B 6/484* (2013.01); *A61B 6/541* (2013.01); *A61B 6/582* (2013.01); *A61N 5/107* (2013.01); *A61N 5/1049* (2013.01); *A61N 5/1067* (2013.01); *A61N 5/1071* (2013.01); *A61N 5/1082* (2013.01); *A61N 2005/1085* (2013.01); *A61N 2005/1091* (2013.01); *A61N 2005/1095* (2013.01); *G06T 7/30* (2017.01); *G06T 11/008* (2013.01); *G06T 2207/10081* (2013.01); *G06T 2210/41* (2013.01); *G06T 2211/404* (2013.01); *G06T 2211/412* (2013.01); *G06T 2211/424* (2013.01); *G06T 2211/428* (2013.01); *G06T 2211/432* (2013.01)

(58) Field of Classification Search
CPC .... A61N 2005/1091; A61N 2005/1095; A61N 5/1081; A61N 5/1049; A61N 5/1042; A61N 2005/1061; A61B 6/4283; A61B 6/4028; A61B 6/541; A61B 6/4021; A61B 6/405; A61B 6/5205; A61B 6/025; A61B 6/027; A61B 6/4435; A61B 6/482; A61B 6/469; A61B 6/481; A61B 6/484; A61B 6/035; A61B 6/4014; A61B 6/5282; A61B 6/582; A61B 5/055; A61B 6/032; A61B 6/0407; A61B 6/06; A61B 6/4078; A61B 6/4085; A61B 6/4441; A61B 6/4458; A61B 6/485; A61B 6/488; A61B 6/08; A61B 6/4064; A61B 6/483; A61B 6/03; A61B 8/488; A61B 6/545; A61B 6/542; A61B 6/0487; A61B 6/4258; A61B 6/5235; A61B 6/5264; A61B 6/4233; A61B 6/5258; A61B 6/50; G06T 7/30; G06T 11/008; G06T 11/005; G06T 2211/404; G06T 2211/412; G06T 2207/10081; G06T 2210/41; G06T 2211/432; G06T 2211/424; G06T 2211/428

See application file for complete search history.

(56) References Cited

U.S. PATENT DOCUMENTS

| | | |
|---|---|---|
| 6,233,478 B1 | 5/2001 | Liu |
| 6,307,909 B1 | 10/2001 | Flohr et al. |
| 7,050,528 B2 | 5/2006 | Chen |
| 7,336,759 B2 | 2/2008 | Nukui |
| 7,660,380 B2 | 2/2010 | Boese et al. |
| 8,116,430 B1 | 2/2012 | Shapiro et al. |
| 8,467,497 B2 | 6/2013 | Lu et al. |
| 8,588,363 B2 | 11/2013 | Flohr |
| 9,400,332 B2 | 7/2016 | Star-Lack et al. |
| 2003/0076927 A1 | 4/2003 | Shigeyuki et al. |
| 2004/0091079 A1 | 5/2004 | Zapalac |
| 2004/0202360 A1 | 10/2004 | Besson |
| 2005/0053188 A1 | 3/2005 | Gohno |
| 2005/0251029 A1 | 11/2005 | Khamene et al. |
| 2006/0109954 A1 | 5/2006 | Gohno |
| 2006/0262894 A1 | 11/2006 | Bernhadt et al. |
| 2007/0127621 A1 | 6/2007 | Grass et al. |
| 2007/0189444 A1 | 8/2007 | Van Steven-Daal et al. |
| 2008/0103834 A1 | 5/2008 | Reiner |
| 2008/0112532 A1 | 5/2008 | Schlomka et al. |
| 2009/0080603 A1 | 3/2009 | Shukla et al. |
| 2009/0135994 A1 | 5/2009 | Yu et al. |
| 2009/0161826 A1 | 6/2009 | Gertner et al. |
| 2009/0225932 A1 | 9/2009 | Zhu et al. |
| 2009/0283682 A1 | 11/2009 | Star-Lack et al. |
| 2009/0304142 A1 | 12/2009 | Ruimi et al. |
| 2010/0046819 A1 | 2/2010 | Noo et al. |
| 2010/0208964 A1 | 8/2010 | Wiegert et al. |
| 2011/0142312 A1 | 6/2011 | Toth et al. |
| 2011/0255656 A1 | 10/2011 | Star-Lack et al. |
| 2012/0014582 A1 | 1/2012 | Schaefer et al. |
| 2012/0207370 A1 | 8/2012 | Fahimian et al. |
| 2012/0263360 A1 | 10/2012 | Zhu et al. |
| 2012/0294504 A1 | 11/2012 | Kyriakou |
| 2013/0101082 A1 | 4/2013 | Jordan et al. |
| 2013/0294570 A1 | 11/2013 | Hansis |
| 2014/0018671 A1 | 1/2014 | Li et al. |
| 2014/0086383 A1 | 3/2014 | Huwer et al. |
| 2014/0169652 A1 | 6/2014 | Vic et al. |
| 2015/0297165 A1 | 10/2015 | Tanaka et al. |
| 2016/0016009 A1 | 1/2016 | Manzke et al. |
| 2016/0120486 A1 | 5/2016 | Goto et al. |
| 2016/0220844 A1 | 8/2016 | Paysan et al. |
| 2016/0262709 A1 | 9/2016 | Siewerdsen et al. |
| 2017/0000428 A1 | 1/2017 | Goto |
| 2017/0197098 A1 | 7/2017 | Hirasawa et al. |
| 2017/0205360 A1 | 7/2017 | Cinquin et al. |
| 2017/0332982 A1 | 11/2017 | Koehler et al. |
| 2018/0070894 A1 | 3/2018 | Osaki et al. |
| 2018/0192978 A1 | 7/2018 | Naylor |
| 2018/0345042 A1 | 12/2018 | Voronenko et al. |
| 2019/0099149 A1 | 4/2019 | Li |
| 2020/0016432 A1 | 1/2020 | Maolinbay |
| 2020/0121267 A1 | 4/2020 | Deutschmann |
| 2020/0402644 A1 | 12/2020 | Zhou et al. |
| 2021/0165122 A1 | 6/2021 | Morton |

FOREIGN PATENT DOCUMENTS

| | | |
|---|---|---|
| EP | 2383702 A1 | 11/2011 |
| JP | H09 218939 A | 8/1997 |
| JP | 2004 136021 | 5/2004 |
| JP | 2008 036275 | 2/2008 |
| WO | 2005112753 A2 | 12/2005 |

(56) References Cited

FOREIGN PATENT DOCUMENTS

| WO | 2006/078386 A2 | 7/2006 |
| WO | 2010/014288 A1 | 2/2010 |
| WO | 2010/099621 A1 | 9/2010 |
| WO | 2015103184 A1 | 7/2015 |
| WO | 2018/156968 A1 | 8/2018 |
| WO | 2018/183748 A1 | 10/2018 |

OTHER PUBLICATIONS

International Search Report and Written Opinion from PCT/US2019/063071 dated Mar. 18, 2020.
International Search Report and Written Opinion from PCT/US2019/063073 dated Apr. 3, 2020.
International Search Report and Written Opinion from PCT/US2019/063078 dated Oct. 8, 2020.
International Search Report and Written Opinion from PCT/US2019/063083 dated Mar. 16, 2020.
International Search Report and Written Opinion from PCT/US2019/063085 dated Mar. 16, 2020.
Invitation to Pay Additional Fees from PCT/US2019/063086 dated Mar. 26, 2020.
International Search Report and Written Opinion from PCT/US2019/063087 dated Apr. 3, 2020.
International Search Report and Written Opinion from PCT/US2019/063077 dated Mar. 16, 2020.
International Search Report and Written Opinion from PCT/US2019/063076 dated Mar. 16, 2020.
International Search Report and Written Opinion from PCT/US2019/063074 dated Mar. 23, 2020.
International Search Report and Written Opinion from PCT/US2019/063086 dated Nov. 16, 2020.
Kang et al., "Accurate for Head and Neck Cancer Patients Using 2D and 3D Image Guidance", Journal of Applied Clinical Medical Physics, vol. 12, No. 1, Dec. 1, 2011, pp. 86-96, XP055734549.
Ramamurthi et al., "Region of Interest Cone Beam Tomography With Prior CT Data," Conference Record of the 37th Asilomar Conference on Signals, Systems, & Computers, vol. 2, Nov. 9, 2003, pp. 1924-1927.
Spearman, et al. Effect of Automated Attenuation-Based Tube Voltage Selection on Radiation Dose at CT: An Observational Study on a Global Scale11, Radiology, vol. 279, No. Apr. 1, 2016 (Apr. 1, 2016), pp. 167-174, XP055734550.
Vinson et al., "X-Ray Micro-CT With a Displaced Detector Array: Application to Helical Cone-Beam Reconstruction," Medical Physics, vol. 30, No. 10, Oct. 1, 2003, pp. 2758-2761.
Wang et al., "A General Cone-Beam Reconstruction Algorithm," IEEE Transactions on Medical Imaging, vol. 12, No. 3, Sep. 1, 1993.
Wang, "X-Ray Micro-CT With a Displaced Detector Array," Medical Physics, vol. 29, No. 7, Jul. 1, 2002.
Office Action from U.S. Appl. No. 16/694,145 dated Mar. 17, 2021, 10 pages.
Office Action from U.S. Appl. No. 16/694,190 dated Mar. 26, 2021, 9 pages.
Notice of Allowance from U.S. Appl. No. 16/694,190 dated Jun. 23, 2021, 8 pages.
Office Action from U.S. Appl. No. 16/694,192 dated Jun. 10, 2021, 10 pages.
Office Action from U.S. Appl. No. 16/694,202 dated Apr. 9, 2021, 12 pages.
Restriction Requirement from U.S. Appl. No. 16/694,210 dated Jun. 10, 2021, 6 pages.
Office Action from U.S. Appl. No. 16/694,218 dated Apr. 15, 2021, 7 pages.
Office Action from U.S. Appl. No. 16/694,230 dated Apr. 1, 2021, 6 pages.
Clackdoyle, et al., Data consistency conditions for truncated fanbeam and parallel projections, Med. Phys. Feb. 2015, pp. 831-845, vol. 42, No. 2.
Defrise, et al., A solution to the long-object problem in helical cone-beam tomography, Physics in Medicine and Biology, 2000, pp. 623-643, vol. 45.
Hsieh, et al., A novel reconstruction algorithm to extend the CT scan field-of-view, Med. Phys., Sep. 2004, pp. 2385-2391, vol. 31, No. 9.
Katsevich, A., An improved exact filtered backprojection algorithm for spiral computed tomography, Advances in Applied Mathematics, 2004, pp. 691-697, vol. 32.
Kudo et al., Exact and approximate algorithms for helical cone-beam CT, Physics in Medicine and Biology, 2004, pp. 1-26, vol. 49, No. 13.
Kunze, et al., Cone beam reconstruction with displaced flat panel detector, 10th International Meeting on Fully Three-Dimensional Image Reconstruction in Radiology and Nuclear Medicine, 2009, pp. 138-141.
Li et al., Scatter kernel estimation with an edge-spread function method for cone-beam computed tomography imaging, Physics in Medicine and Biology, pp. 6729-6748, vol. 51, 2008.
Maslowski, et al., Acuros CTS: A fast, linear Boltzmann transport equation solver for computed tomography scatter—Part I: Core algorithms and validation, Med. Phys., 2018, pp. 1-15.
Ning, et al., X-ray scatter correction algorithm for cone beam CT imaging, Med. Phys., May 2004, pp. 1195-1202, vol. 31, No. 5.
Noo et al., A new scheme for view-dependent data differentiation in fan-beam and cone-beam computed tomography, Physics in Medicine and Biology, 2007, pp. 5593-5414, vol. 52.
Schäfer, et al., FBP and BPF reconstruction methods for circular X-ray tomography with off-center detector, Med. Phys., Jul. 2011, pp. S85-S94, vol. 38, No. 7.
Schäfer, et al., Cone-beam filtered back-projection for circular X-ray tomography with off-center detector, 10th International Meeting on Fully Three-Dimensional Image Reconstruction in Radiology and Nuclear Medicine, 2009, pp. 86-89.
Siewerdsen, et al., A simple, direct method for x-ray scatter estimation and correction in digital radiography and cone-beam CT, Med. Phys., Jan. 2006, pp. 187-197, vol. 33, No. 1.
Sun, et al., Improved scatter correction using adaptive scatter kernel superposition, Physics in Medicine and Biology, Oct. 2010, pp. 6695-6720, vol. 55.
Tang, et al., A sinogram extrapolation method for CT field of view extension, Proceedings of the Fifth CT Meeting, 2018, pp. 206-209.
Yu, et al., Radiation dose reduction in computed tomography: techniques and future perspective, Imaging Med., Oct. 2009, pp. 65-84, vol. 1.
Zamyatin, et al., Helical cone beam CT with an asymmetrical detector, Medical Physics, Oct. 2005, pp. 3117-3127, vol. 32, No. 10.
Zbijewski, et al., Efficient Monte Carlo Based Scatter Artifact Reduction in Cone-Beam Micro-CT, IEEE Transactions on Medical Imaging, Jul. 2006, pp. 817-827, vol. 25, No. 7.
Zhu, et al., Scatter Correction Method for X-ray CT Using Primary Modulation: Theory and Preliminary Results, IEEE Transactions on Medical Imaging, Dec. 2006, pp. 1573-1587, vol. 25, No. 12.
Zhu, et al. Noise suppression in scatter correction for cone-beam CT, American Association of Physicists in Medicine, 2009, pp. 741-752, vol. 36, No. 3.
Office Action from U.S. Appl. No. 16/694,161 dated Sep. 13, 2021, 18 pages.

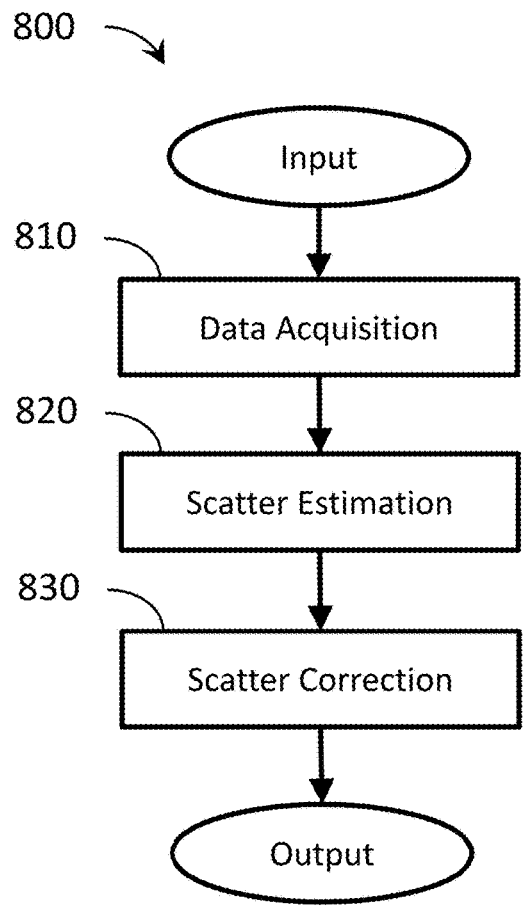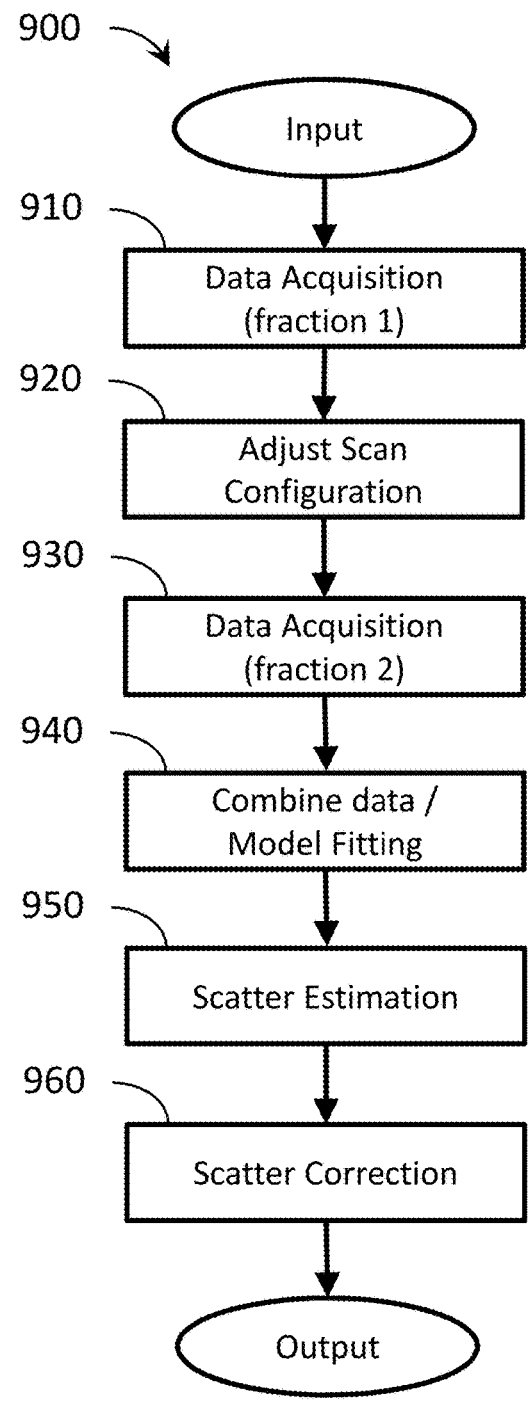
FIG. 8
FIG. 9

METHOD AND APPARATUS FOR IMAGE RECONSTRUCTION AND CORRECTION USING INTER-FRACTIONAL INFORMATION

CROSS-REFERENCE TO RELATED APPLICATIONS

This application claims the benefit of eleven U.S. provisional patent applications, including Ser. No. 62/773,712, filed Nov. 30, 2018; Ser. No. 62/773,700, filed Nov. 30, 2018; Ser. No. 62/796,831, filed Jan. 25, 2019; Ser. No. 62/800,287, filed Feb. 1, 2019; Ser. No. 62/801,260, filed Feb. 5, 2019; Ser. No. 62/813,335, filed Mar. 4, 2019; Ser. No. 62/821,116, filed Mar. 20, 2019; Ser. No. 62/836,357, filed Apr. 19, 2019; Ser. No. 62/836,352, filed Apr. 19, 2019; Ser. No. 62/843,796, filed May 6, 2019; and Ser. No. 62/878,364, filed Jul. 25, 2019. This application is also related to ten non-provisional U.S. patent applications filed on the same day, including Ser. No. 16/694,145, filed Nov. 25, 2019, entitled "MULTIMODAL RADIATION APPARATUS AND METHODS;" Ser. No. 16/694,148, filed Nov. 25, 2019, entitled "APPARATUS AND METHODS FOR SCALABLE FIELD OF VIEW IMAGING USING A MULTI-SOURCE SYSTEM;" Ser. No. 16/694,161, filed Nov. 25, 2019, entitled "INTEGRATED HELICAL FAN-BEAM COMPUTED TOMOGRAPHY IN IMAGE-GUIDED RADIATION TREATMENT DEVICE;" Ser. No. 16/694,166, filed Nov. 25, 2019, entitled "COMPUTED TOMOGRAPHY SYSTEM AND METHOD FOR IMAGE IMPROVEMENT USING PRIOR IMAGE;" Ser. No. 16/694,177, filed Nov. 25, 2019, entitled "OPTIMIZED SCANNING METHODS AND TOMOGRAPHY SYSTEM USING REGION OF INTEREST DATA;" Ser. No. 16/694,190, filed Nov. 25, 2019, entitled "HELICAL CONE-BEAM COMPUTED TOMOGRAPHY IMAGING WITH AN OFF-CENTERED DETECTOR;" Ser. No. 16/694,192, filed Nov. 25, 2019, entitled "MULTI-PASS COMPUTED TOMOGRAPHY SCANS FOR IMPROVED WORKFLOW AND PERFORMANCE;" Ser. No. 16/694,202, filed Nov. 25, 2019, entitled "METHOD AND APPARATUS FOR SCATTER ESTIMATION IN CONE-BEAM COMPUTED TOMOGRAPHY;" Ser. No. 16/694,210, filed Nov. 25, 2019, entitled "ASYMMETRIC SCATTER FITTING FOR OPTIMAL PANEL READOUT IN CONE-BEAM COMPUTED TOMOGRAPHY;" Ser. No. 16/694,218, filed Nov. 25, 2019, entitled "METHOD AND APPARATUS FOR IMPROVING SCATTER ESTIMATION AND CORRECTION IN IMAGING." The contents of all above-identified patent application(s) and patent(s) are fully incorporated herein by reference.

FIELD OF THE INVENTION

Aspects of the disclosed technology relate to computed tomography imaging, and in particular, to image reconstruction and correction in projection data, and, more particularly, to an apparatus and method utilizing inter-fractional information to estimate scatter in primary region projection data during computed tomography (CT) scans.

BACKGROUND

Scatter in cone-beam CT can account for a significant portion of the detected photons (including when no anti-scatter grids are used) with a wide collimation opening. Scatter can negatively impact image quality, including contrast and quantitative accuracy. Consequently, scatter measurement and scatter correction are applicable to cone-beam CT data processing and image reconstruction, including in the context of image-guided radiation treatment (IGRT). IGRT can make use of medical imaging technology, such as CT, to collect images of a patient before, during, and/or after treatment.

Most scatter measurement and correction approaches fall into the following categories. In the first category are the model-based methods. These methods model both a data acquisition system and the interaction process between x-rays and materials. The former requires detailed knowledge of the major components of the entire imaging chain as well as information of the patient, which may be obtained from a planning CT or a first-pass reconstruction without scatter correction. These methods can either be realized stochastically (e.g., Monte-Carlo-simulation based approaches) or deterministically (e.g., radiative-transfer-equation based approaches). The former is computationally costly, and the latter is generally considered as an open problem in the field. The model-based methods are typically patient specific and more accurate. However, these methods require a considerable amount of prior information on the data acquisition system and the patient, such that the effectiveness of these methods is highly dependent on the modeling accuracy. Furthermore, they are also highly demanding in terms of computational power and time resulting in a significant negative impact on workflow and throughput.

In the second category are the deconvolution-kernel based methods. Measured x-ray projection data are considered a convolution result of the primary and the scatter kernels. These methods perform a deconvolution process to separate the primary and scatter by using appropriate kernels that are established ahead of time. These methods are practical and effective to a certain extent. However, they are sensitive to the kernel design, especially in terms of material and shape of the scanned object.

In the third category are the direct-measurement based methods, such as beam-stopper-array and primary modulation. These methods are capable of measuring scatter while acquiring projection data. They do not require prior information, and thus are very robust and practical. Drawbacks of such methods include wasted dose and/or degraded image quality.

Another direct-measurement based method measures scatter from a shadowed region of the detector in the longitudinal direction, which is then further used for estimation of the scatter located inside the collimation opening (primary region). However, this method is designed for a single circular scan (i.e., measurements in the primary and scatter regions occur concurrently during the same rotation), requires detector availability outside on both sides (in the longitudinal direction) of the collimation opening, and is limited in terms of estimation accuracy.

BRIEF SUMMARY

In one embodiment, a method of estimating scatter during imaging across multiple fractions includes receiving a previous fraction scatter measurement from a previous fraction, receiving a current fraction scatter measurement from a current fraction, wherein a scatter-to-primary ratio during the current fraction is greater than during the previous fraction, and determining a current fraction scatter estimate based on the current fraction scatter measurement and the previous fraction scatter measurement.

Features that are described and/or illustrated with respect to one embodiment may be used in the same way or in a similar way in one or more other embodiments and/or in combination with or instead of the features of the other embodiments.

The descriptions of the invention do not limit the words used in the claims in any way or the scope of the claims or invention. The words used in the claims have all of their full ordinary meanings.

BRIEF DESCRIPTION OF THE DRAWINGS

In the accompanying drawings, which are incorporated in and constitute a part of the specification, embodiments of the invention are illustrated, which, together with a general description of the invention given above, and the detailed description given below, serve to exemplify embodiments of this invention. It will be appreciated that illustrated element boundaries (e.g., boxes, groups of boxes, or other shapes) in the figures represent one embodiment of boundaries. In some embodiments, one element may be designed as multiple elements or that multiple elements may be designed as one element. In some embodiments, an element shown as an internal component of another element may be implemented as an external component and vice versa. Furthermore, elements may not be drawn to scale.

FIG. 8 is a flow chart depicting an exemplary method of scatter estimation and correction using inter-fractional data.

FIG. 9 is a flow chart depicting another exemplary method of scatter estimation and correction using inter-fractional data.

DETAILED DESCRIPTION

Figure 1:
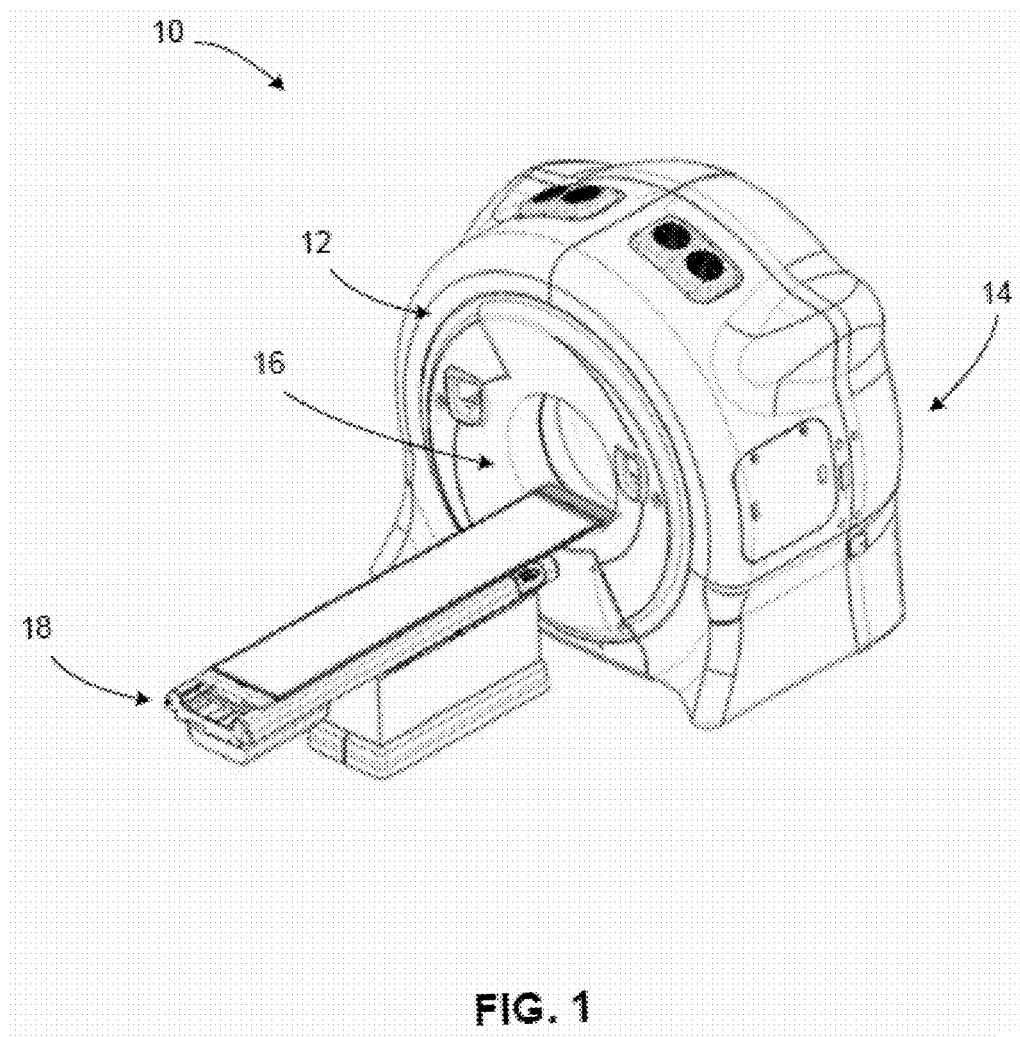
FIG. 1 is a perspective view of an exemplary imaging apparatus in accordance with one aspect of the disclosed technology.

The following includes definitions of exemplary terms that may be used throughout the disclosure. Both singular and plural forms of all terms fall within each meaning.

"Component," as used herein can be defined as a portion of hardware, a portion of software, or a combination thereof. A portion of hardware can include at least a processor and a portion of memory, wherein the memory includes an instruction to execute. A component may be associated with a device.

"Logic," synonymous with "circuit" as used herein, includes but is not limited to hardware, firmware, software and/or combinations of each to perform a function(s) or an action(s). For example, based on a desired application or needs, logic may include a software-controlled microprocessor, discrete logic such as an application specific integrated circuit (ASIC), or other programmed logic device and/or controller. Logic may also be fully embodied as software.

"Processor," as used herein includes, but is not limited to, one or more of virtually any number of processor systems or stand-alone processors, such as microprocessors, microcontrollers, central processing units (CPUs), and digital signal processors (DSPs), in any combination. The processor may be associated with various other circuits that support operation of the processor, such as random-access memory (RAM), read-only memory (ROM), programmable read-only memory (PROM), erasable programmable read-only memory (EPROM), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

"Signal," as used herein includes, but is not limited to, one or more electrical signals, including analog or digital signals, one or more computer instructions, a bit or bit stream, or the like.

"Software", as used herein, includes but is not limited to one or more computer readable and/or executable instructions that cause a computer, processor, logic, and/or other electronic device to perform functions, actions, and/or behave in a desired manner. The instructions may be embodied in various forms such as routines, algorithms, modules, or programs including separate applications or code from dynamically linked sources or libraries.

While the above exemplary definitions have been provided, it is Applicant's intention that the broadest reasonable interpretation consistent with this specification be used for these and other terms.

As is discussed in more detail below, embodiments of the disclosed technology relate to multi-pass scans for improved workflow and/or performance. In some embodiments, a radiotherapy delivery device and method can make use of an integrated low-energy radiation source for CT for use in conjunction with or as part of IGRT. In particular, for example, a radiotherapy delivery device and method can combine a low-energy collimated radiation source for imaging in a gantry using rotational image acquisition along with a high-energy radiation source for therapeutic treatment. In some embodiments, the low-energy radiation source (e.g., kV) can produce higher quality images than via use of the high-energy radiation source (e.g., MV) for imaging. Images generated with kV energy can have better tissue contrast than with MV energy. High quality volume imaging can be needed for visualization of targets and organs-at-risk (OARS), for adaptive therapy monitoring, and for treatment planning/re-planning. In some embodiments, the kV imaging system can also be used for positioning, motion tracking, and/or characterization or correction capabilities.

The image acquisition methodology can include or otherwise make use of a multiple rotation scan, which may be, for example, a continuous scan (e.g., with a helical source trajectory about a central axis together with longitudinal movement of a patient support through a gantry bore), a non-continuous circular stop-and-reverse scan with incremental longitudinal movement of a patient support, etc.

In accordance with various embodiments, the imaging apparatus collimates a radiation source, including, for example, into a cone beam or a fan beam using, for example, a beamformer. In one embodiment, the collimated beam can be combined with a gantry that continuously rotates while the patient moves, resulting in a helical image acquisition.

In some embodiments, the time associated with increased scanning rotations to complete a high-quality volume image may be mitigated by high gantry rates/speed (e.g., using fast slip ring rotation, including, e.g., up to 10 revolutions per minute (rpm), up to 20 rpm, up to 60 rpm, or more rpm), high kV frame rates, and/or sparse data reconstruction techniques, to provide kV CT imaging on a radiation therapy delivery platform. Detectors (with various row/slice sizes, configurations, dynamic range, etc.), scan pitch, and/or dynamic collimation are additional features in various embodiments, including to selectively expose portions of the detector and selectively define active readout areas.

A helical scan trajectory can have several advantages in view of a circular scan. For example, cone-beam artifacts are reduced because a helical scan can provide more complete projection data for image reconstruction. Also, a helical scan can acquire projection data for a large longitudinal coverage with a narrow axial opening, which could substantially reduce scatter contamination in the projection data. Reconstructed images can have significantly improved image quality in terms of low frequency artifacts and result in greatly enhanced soft-tissue contrast. Furthermore, a helical scan can improve scan speed with a large pitch.

Figure 2:
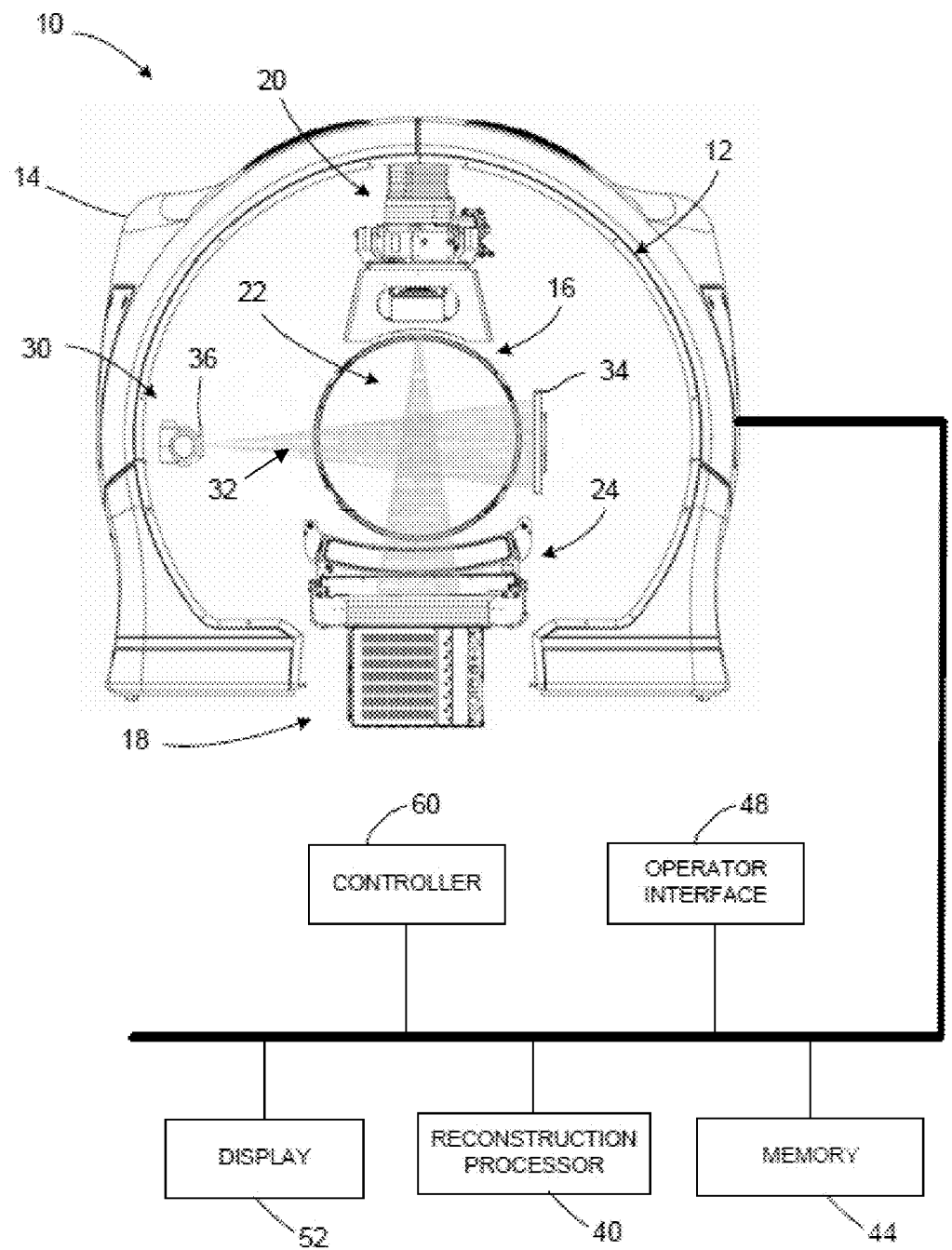
FIG. 2 is a diagrammatic illustration of an imaging apparatus integrated into an exemplary radiotherapy device in accordance with one aspect of the disclosed technology.

With reference to FIG. 1 and FIG. 2, an imaging apparatus 10 (e.g., an x-ray imaging apparatus) is shown. It will be appreciated that the x-ray imaging apparatus 10 may be associated with and/or integrated into a radiotherapy device (as shown in FIG. 2) that can be used for a variety of applications, including, but not limited to IGRT. The x-ray imaging apparatus 10 includes a rotatable gantry system, referred to as gantry 12 supported by or otherwise housed in a support unit or housing 14. Gantry herein refers to a gantry system that comprises one or more gantries (e.g., ring or C-arm) capable of supporting one or more radiation sources and/or associated detectors as they rotate around a target. For example, in one embodiment, a first radiation source and its associated detector may be mounted to a first gantry of the gantry system and a second radiation source and its associated detector may be mounted to a second gantry of the gantry system. In another embodiment, more than one radiation source and associated detector(s) may be mounted to the same gantry of the gantry system, including, for example, where the gantry system is comprised of only one gantry. Various combinations of gantries, radiation sources, and radiation detectors may be combined into a variety of gantry system configurations to image and/or treat the same volume within the same apparatus. For example, kV and MV radiation sources can be mounted on the same or different gantries of the gantry system and selectively used for imaging and/or treatment as part of an IGRT system. If mounted to different gantries, the radiation sources are able to rotate independently, but are still able to simultaneously image the same (or nearly the same) volume. A rotatable ring gantry 12 may be capable of 10 rpm or more, as mentioned above. The rotatable gantry 12 defines a gantry bore 16 into and through which a patient can be moved and positioned for imaging and/or treatment. In accordance with one embodiment, the rotatable gantry 12 is configured as a slip ring gantry to provide continuous rotation of an imaging radiation source (e.g., x-ray) and an associated radiation detector while providing sufficient bandwidth for the high-quality imaging data received by the detector. A slip-ring gantry can eliminate gantry rotations in alternating directions in order to wind and unwind cables carrying the power and signals associated with the device. Such a configuration will allow for continuous helical (e.g., fan-beam, cone-beam, etc.) computed tomography, even when integrated into an IGRT system.

A patient support 18 or table/couch is positioned adjacent to the rotatable gantry 12 and configured to support a patient, typically in a horizontal position, for longitudinal movement into and within the rotatable gantry 12. The patient support 18 can move the patient, for example, in a direction perpendicular to the plane of rotation of the gantry 12 (along or parallel to the rotation axis of the gantry 12). The patient support 18 can be operatively coupled to a patient support controller for controlling movement of the patient and patient support 18. The patient support controller can be synchronized with the rotatable gantry 12 and sources of radiation mounted to the rotating gantry for rotation about a patient longitudinal axis in accordance with a commanded imaging and/or treatment plan. In some embodiments, the patient support can also be moved in a limited range up and down, left and right once it is in the bore 16 to adjust the patient position for optimal treatment.

As shown in FIG. 2, the x-ray imaging apparatus 10 includes a source of imaging radiation 30 coupled to or otherwise supported by the rotatable gantry 12. The source of imaging radiation 30 emits a radiation beam (indicated generally as 32) for generating high-quality images. In this embodiment, the source of imaging radiation is an x-ray source 30, configured as a kilovoltage (kV) source (e.g., a clinical x-ray source having an energy level in the range of about 20 kV to about 150 kV). In one embodiment, the kV source of radiation comprises a kilo-electron volt peak photon energy (keV) up to 150 keV. The imaging radiation source can be any type of transmission source suitable for imaging. For example, the imaging radiation source may be, for example, an x-ray generating source (including for CT) or any other way to produce photons with sufficient energy and flux (such as, e.g., a gamma-source (e.g., Cobalt-57, energy peak at 122 keV), an x-ray fluorescence source (such as fluorescence source through Pb k lines, two peaks @about 70 keV and @about 82 keV), etc.). References herein to x-ray, x-ray imaging, x-ray imaging source, etc. are exemplary for particular embodiments. Other imaging transmission sources can be used interchangeably in various other embodiments.

A detector 34 (e.g., two-dimensional flat detector or curved detector) can be coupled to or otherwise supported by the rotatable gantry 12. The x-ray detector 34 is positioned to receive radiation from the x-ray source 30 and can rotate along with the x-ray source 30. The detector 34 can detect or otherwise measure the amount of radiation not attenuated and therefore infer what was in fact attenuated by the patient or associated patient ROI (by comparison to what was initially generated). The detector 34 can detect or otherwise collect attenuation data from different angles as the x-ray source 30 rotates around and emits radiation toward the patient.

It will be appreciated that the x-ray detector 34 can take on a number of configurations without departing from the scope of the disclosed technology. As illustrated in FIG. 2, the x-ray detector 34 can be configured as a flat-panel detector (e.g., a multi-row flat panel detector). In accordance with another exemplary embodiment, the x-ray detector 34 can be configured as a curved detector. The detector 34 can be adjusted to an offset (i.e., shifted) position in the channel and/or axial direction.

Although FIGS. 1 and 2 depict an x-ray imaging apparatus 10 with a radiation source 30 mounted to a ring gantry 12, other embodiments may include other types of rotatable imaging apparatuses, including, for example, C-arm gantries and robotic arm-based systems. In gantry-based systems, a gantry rotates the imaging radiation source 30 around an axis passing through the isocenter. Gantry-based systems include C-arm gantries, in which the imaging radiation source 30 is mounted, in a cantilever-like manner, over and rotates about the axis passing through the isocenter. Gantry-based systems further include ring gantries, for example, rotatable gantry 12, having generally toroidal shapes in which the patient's body extends through a bore of the ring/toroid, and the imaging radiation source 30 is mounted on the perimeter of the ring and rotates about the axis passing through the isocenter. In some embodiments, the gantry 12 rotates continuously. In other embodiments, the gantry 12 utilizes a cable-based system that rotates and reverses repeatedly.

A collimator or beamformer assembly (indicated generally as 36) is positioned relative to the x-ray source 30 to selectively control and adjust a shape of a radiation beam 32 emitted by the x-ray source 30 to selectively expose a portion or region of the active area of the x-ray detector 34. The beamformer can also control how the radiation beam 32 is positioned on the x-ray detector 34. In one embodiment, the beamformer 36 could have one degree/dimension of motion (e.g., to make a thinner or fatter slit). In another embodiment, the beamformer 36 can have two degrees/dimensions of motion (e.g., to make various sized rectangles). In other embodiments, the beamformer 36 may be capable of various other dynamically-controlled shapes, including, for example, parallelograms. All of these shapes may be dynamically adjusted during a scan. In some embodiments, blocking portions of the beamformer can be rotated and translated.

The beamformer 36 can be controlled to adjust the shape of the radiation beam 32 emitted by the x-ray source 30 dynamically in a number of geometries, including, but not limited to, a fan beam or cone beam having a beam thickness (width) as low as one detector row width or including multiple detector rows, which will be only a portion of the detector's active area. In various embodiments, the thickness of the beam may expose several centimeters of a larger detector active area. For example, 3-4 centimeters (measured in the longitudinal direction in the detector plane) of a 5-6 centimeter detector may be selectively exposed to the imaging radiation 32. In this embodiment, 3-4 centimeters of projection image data may be captured with each readout, with about 1-2 centimeters of unexposed detector area on one or each side, which may be used to capture scatter data, as discussed below.

In other embodiments, more or less of a portion of the active detector may be selectively exposed to the imaging radiation. For example, in some embodiments, the beam thickness may be reduced down to about two centimeters, one centimeter, less than one centimeter, or ranges of similar sizes, including with smaller detectors. In other embodiments, the beam thickness may be increased to about 4 centimeters, 5 centimeters, greater than 5 centimeters, or ranges of similar sizes, including with larger detectors. In various embodiments, the ratio of exposed-to-active detector area may be 30-90% or 50-75%. In other embodiments, the ratio of exposed-to-active detector area may be 60-70%. However, various other exposed and active area sizes or ratios of exposed-to-active detector area may be suitable in other embodiments. The beam and detector can be configured so that the shadowed region of the detector (active but not exposed to direct radiation) is sufficient to capture scatter data beyond the penumbra region.

Various embodiments may include an optimization of the features that control selective exposure of the detector 34 (e.g., beam size, beam/aperture center, collimation, pitch, detector readout range, detector readout center, etc.) such that the measured data is sufficient for primary (exposed) and shadowed regions, but also optimized for speed and dosage control. The beamformer 36 shape/position and detector 34 readout range can be controlled such that the radiation beam 32 from the x-ray source 30 covers as much or as little of the x-ray detector 34 based on the particular imaging task being carried out. The beam 32 can be shaped to be various shapes, including, for example, parallelograms. The beamformer 36 can be configured to adjust the shape of the radiation beam 32 by rotation and/or translation of x-ray attenuated material of the beamformer 36.

The collimator/beamformer 36 may be configured in a variety of ways that allow it to adjust the shape of the radiation beam 32 emitted by the x-ray source 30. For example, the collimator 36 can be configured to include a set of jaws or other suitable members that define and selectively adjust the size of an aperture through which the radiation beam from the x-ray source 30 may pass. In accordance with one exemplary configuration, the collimator 36 can include an upper jaw and a lower jaw, where the upper and lower jaws are movable in different directions (e.g., parallel directions) to adjust the size of the aperture through which the radiation beam from the x-ray source 30 passes, and also to adjust the beam position relative to the patient to illuminate only the portion of the patient to be imaged for optimized imaging and minimized patient dose.

In accordance with one embodiment, the shape of the radiation beam 32 from the x-ray source 30 can be changed during an image acquisition. Stated differently, in accordance with one exemplary implementation, the beamformer 36 leaf positions and/or aperture width can be adjusted before or during a scan. For example, in accordance with one embodiment, the beamformer 36 can be selectively controlled and dynamically adjusted during rotation of the x-ray source 30 such that the radiation beam 32 has a shape with sufficient primary/shadow regions and is adjusted to include only an object of interest during imaging (e.g., the prostate). The shape of the radiation beam 32 being emitted by the x-ray source 30 can be changed during or after a scan, depending on the desired image acquisition, which may be based on imaging and/or therapeutic feedback, as discussed in more detail below.

As shown in FIG. 2, the x-ray imaging apparatus 10 may be integrated with a radiotherapy device that includes a therapeutic radiation source 20 coupled to or otherwise supported by the rotatable gantry 12. In accordance with one embodiment, the therapeutic radiation source 20 is configured as a source of therapeutic radiation, such as a high-energy source of radiation used for treatment of a tumor within a patient in a region of interest. It will be appreciated that the source of therapeutic radiation can be a high-energy x-ray beam (e.g., megavoltage (MV) x-ray beam), and/or a high-energy particle beam (e.g., a beam of electrons, a beam of protons, or a beam of heavier ions, such as carbon) or another suitable form of high-energy radiation. In one embodiment, the first source of radiation 20 comprises a mega-electron volt peak photon energy (MeV) of 1 MeV or greater. In one embodiment, the high-energy x-ray beam has an average energy greater than 0.8 MeV. In another embodiment, the high-energy x-ray beam has an average energy greater than 0.2 MeV. In another embodiment, the high-energy x-ray beam has an average energy greater than 150 keV. Generally, the first source of radiation 20 has a higher energy level (peak and/or average, etc.) than the second source of radiation 30.

In one embodiment, the therapeutic radiation source 20 is a linear accelerator (LINAC) producing therapeutic radiation (e.g., MV source) and the imaging system comprises an independent x-ray imaging source of radiation producing relatively low intensity and lower energy imaging radiation (e.g., kV source). In other embodiments, the therapeutic radiation source 20 could be a radioisotope, such as, for example, Co-60, and it can generally have energy >1 MeV. The therapeutic radiation source 20 can emit one or more beams of radiation (indicated generally by 22) toward a region-of-interest (ROI) within a patient supported on the patient support 18 in accordance with a treatment plan. In some embodiments, the therapeutic radiation source 20 may be used for imaging.

Detector 24 can be coupled to or otherwise supported by the rotatable gantry 12 and positioned to receive radiation 22 from the therapeutic radiation source 20. The detector 24 can detect or otherwise measure the amount of radiation not attenuated and therefore infer what was in fact attenuated by the patient or associated patient ROI (by comparison to what was initially generated). The detector 24 can detect or otherwise collect attenuation data from different angles as the therapeutic radiation source 20 rotates around and emits radiation toward the patient.

It will be further appreciated that the therapeutic radiation source 20 can include or otherwise be associated with a collimator. The collimator associated with the therapeutic radiation source 20 can be configured in a number of ways, similar to the collimator/beamformer 36 associated with the imaging source 30. For example, a collimator/beamformer can be configured as a multi-leaf collimator (MLC), which can include a plurality of interlaced leaves operable to move to one or more positions between a minimally-open or closed position and a maximally-open position. It will be appreciated that the leaves can be moved into desired positions to achieve a desired shape of a radiation beam being emitted by the radiation source. In one embodiment, the MLC is capable of sub-millimeter targeting precision.

The therapeutic radiation source 20 may be mounted, configured, and/or moved into the same plane or a different plane (offset) than the imaging source 30. In some embodiments, scatter caused by simultaneous activation of the radiation sources 20, 30 may be reduced by offsetting the radiation planes.

When integrated with a radiotherapy device, x-ray imaging apparatus 10 can provide images that are used to set up (e.g., align and/or register), plan, and/or guide a radiation delivery procedure (treatment). Typical set-up is accomplished by comparing current (in-treatment) images to pre-treatment image information. Pre-treatment image information may comprise, for example, computed tomography (CT) data, cone-beam CT data, magnetic resonance imaging (MRI) data, positron emission tomography (PET) data or 3D rotational angiography (3DRA) data, and/or any information obtained from these or other imaging modalities. In some embodiments, the x-ray imaging apparatus 10 can track in-treatment patient, target, or ROI motion.

A reconstruction processor 40 can be operatively coupled to detector 24 and/or x-ray detector 34. In one embodiment, the reconstruction processor 40 is configured to generate patient images based on radiation received by the x-ray detector 34 from the x-ray source 30. It will be appreciated that the reconstruction processor 40 can be configured to be used to carry out the methods described more fully below. The apparatus also includes a memory 44 suitable for storing information, including, but not limited to, processing and reconstruction algorithms and software, imaging parameters, image data from a prior or otherwise previously-acquired image (e.g., a planning image), treatment plans, and the like.

The x-ray imaging apparatus 10 can include an operator/user interface 48, where an operator of the x-ray imaging apparatus 10 can interact with or otherwise control the x-ray imaging apparatus 10 to provide input relating to scan or imaging parameters and the like. The operator interface 48 can include any suitable input devices, such as a keyboard, mouse, voice-activated controller, or the like. The x-ray imaging apparatus 10 can also include a display 52 or other human-readable element to provide output to the operator of the x-ray imaging apparatus 10. For example, the display 52 can allow the operator to observe reconstructed patient images and other information, such as imaging or scan parameters, related to operation of the x-ray imaging apparatus 10.

As shown in FIG. 2, the x-ray imaging apparatus 10 includes a controller (indicated generally as 60) operatively coupled to one or more components of the apparatus 10. The controller 60 controls the overall functioning and operation of apparatus 10, including providing power and timing signals to the x-ray source 30 and/or the therapeutic radiation source 20 and a gantry motor controller that controls rotational speed and position of the rotatable gantry 12. It will be appreciated that the controller 60 can encompass one or more of the following: a patient support controller, a gantry controller, a controller coupled to the therapeutic radiation source 20 and/or the x-ray source 30, a beamformer 36 controller, a controller coupled to the detector 24 and/or the x-ray detector 34, and the like. In one embodiment controller 60 is a system controller that can control other components, devices, and/or controllers.

In various embodiments, the reconstruction processor 40, the operator interface 48, the display 52, the controller 60 and/or other components may be combined into one or more components or devices.

The apparatus 10 may include various components, logic, and software. In one embodiment, the controller 60 comprises a processor, a memory, and software. By way of example and not limitation, an x-ray imaging apparatus and/or radiotherapy system can include various other devices and components (e.g., gantries, radiation sources, collimators, detectors, controllers, power sources, patient supports, among others) that can implement one or more routines or steps related to imaging and/or IGRT for a specific application, wherein a routine can include imaging, image-based pre-delivery steps, and/or treatment delivery, including respective device settings, configurations, and/or positions (e.g., paths/trajectories), which may be stored in memory. Furthermore, the controller(s) can directly or indirectly control one or more devices and/or components in accordance with one or more routines or processes stored in memory. An example of direct control is the setting of various radiation source or collimator parameters (power, speed, position, timing, modulation, etc.) associated with imaging or treatment. An example of indirect control is the communication of position, path, speed, etc. to a patient support controller or other peripheral device. The hierarchy of the various controllers that may be associated with an x-ray imaging apparatus can be arranged in any suitable manner to communicate the appropriate commands and/or information to the desired devices and components.

Moreover, those skilled in the art will appreciate that the systems and methods may be implemented with other computer system configurations. The illustrated aspects of the invention may be practiced in distributed computing environments where certain tasks are performed by local or remote processing devices that are linked through a communications network. For example, in one embodiment, the reconstruction processor 40 may be associated with a separate system. In a distributed computing environment, program modules may be located in both local and remote memory storage devices. For instance, a remote database, a local database, a cloud-computing platform, a cloud database, or a combination thereof can be utilized with x-ray imaging apparatus 10.

X-ray imaging apparatus 10 can utilize an exemplary environment for implementing various aspects of the invention including a computer, wherein the computer includes the controller 60 (e.g., including a processor and a memory, which may be memory 44) and a system bus. The system bus can couple system components including, but not limited to the memory to the processor, and can communicate with other systems, controllers, components, devices, and processors. Memory can include read only memory (ROM), random access memory (RAM), hard drives, flash drives, and any other form of computer readable media. Memory can store various software and data, including routines and parameters, which may comprise, for example, a treatment plan.

The therapeutic radiation source 20 and/or x-ray source 30 can be operatively coupled to a controller 60 configured to control the relative operation of the therapeutic radiation source 20 and the x-ray source 30. For example, the x-ray source 30 can be controlled and operated simultaneously with the therapeutic radiation source 20. In addition, or alternatively, the x-ray source 30 can be controlled and operated sequentially with the therapeutic radiation source 20, depending on the particular treatment and/or imaging plan being implemented.

It will be appreciated that the x-ray source 30 and the x-ray detector 34 can be configured to provide rotation around the patient during an imaging scan in a number of ways. In one embodiment, synchronizing the motion and exposure of the x-ray source 30 with the longitudinal motion of the patient support 18 can provide a continuous helical acquisition of a patient image during a procedure. In addition to continuous rotation of the radiation sources 20, 30 and detector(s) 24, 34 (e.g., continuous and constant rotation of the gantry with constant patient motion speed), it will be appreciated that other variations can be employed without departing from the scope of the disclosed technology. For example, the rotatable gantry 12 and patient support can be controlled such that the gantry 12 rotates in a "back-and-forth" manner (e.g., alternating clockwise rotation and counterclockwise rotation) around a patient supported on the patient support (as opposed to continuously, as is described above) as the support is controlled to move (at a constant or variable speed) relative to the rotatable gantry 12. In another embodiment, with successive step-and-shoot circular scans, movement of the patient support 18 in the longitudinal direction (step) alternates with a scanning revolution by the rotatable gantry 12 (shoot) until the desired volume is captured.

Various other types of radiation source and/or patient support movement may be utilized to achieve relative motion of the radiation source and the patient for generation of projection data. Non-continuous motion of the radiation source and/or patient support, continuous but variable/non-constant (including linear and non-linear) movement, speed, and/or trajectories, etc., and combinations thereof may be used, including in combination with the various embodiments of radiotherapy devices 10 described above.

Generally, a treatment course for a patient can comprise multiple fractions. In various embodiments, the entire treatment course as a whole can utilize inter-fractional information to optimize image reconstruction and correction, including scatter estimation. For example, this may include performing a fine scatter estimation at the beginning of the treatment course. In subsequent fractions, the scan configuration can gradually change for improved workflow and reduced patient dose, albeit with possibly degraded scatter measurement (i.e., an increase in the scatter-to-primary data ratio). The scatter content generally increases with larger beam widths and the sampling of its distribution can become sparser (less precise) with larger beam widths, resulting in an increase in the scatter-to-primary ratio. As discussed in detail below, adjusting (e.g., loosening or tightening) scan configurations (e.g., via scan parameter settings), for example, to improve workflow and/or reduce patient dose, can affect the scatter to primary data ratio. Although scatter measurement from a loosened configuration may be associated with a higher scatter-to-primary ratio when compared to a measurement from a previous fraction, the quality of scatter estimation for the current fraction may still be adequate. For example, the quality of the scatter estimation with a higher scatter-to-primary ratio may be reduced but adequate, the same as a previous fraction, or improved, by combining scatter estimations from previous fractions, for at least two reasons. First, scatter can be very low frequency and is expected to change little from fraction to fraction, and thus the very fine scatter estimation from the first fraction can still be considered as valid for the scatter of the current fraction. Second, across different fractions, more scatter measurements are generated, and thus more data is available for scatter estimation, which has the potential to improve scatter estimation and exclude outliers.

This technique can work well if the patient shape is stable, which is true for a hypofractionation treatment that includes a small number of fractions (e.g., about 5), but may not work well in a conventional fractionation that includes a large number of fractions (e.g., about 30). Therefore, in some embodiments, patient information, such as weight, body mass index (BMI), shape, etc., can also be monitored from fraction to fraction. Once a substantial change is observed in the patient, a fine scan configuration can be reactivated, and the inter-fractional process can restart.

In some embodiments, this technique can be integrated into an adaptive workflow, where the adaptive software can flag the user that the quality of the fine scan scatter estimate is reduced.

The following flow charts and block diagrams illustrate exemplary configurations and methodologies associated with scatter estimation in accordance with the systems described above. The exemplary methodologies may be carried out in logic, software, hardware, or combinations thereof. In addition, although the procedures and methods are presented in an order, the blocks may be performed in different orders, including series and/or parallel. Thus, the steps below, including imaging, image-based pre-delivery steps, and treatment delivery, although shown sequentially, may be executed simultaneously, including in real-time. Further, additional steps or fewer steps may be used.

Figure 3:
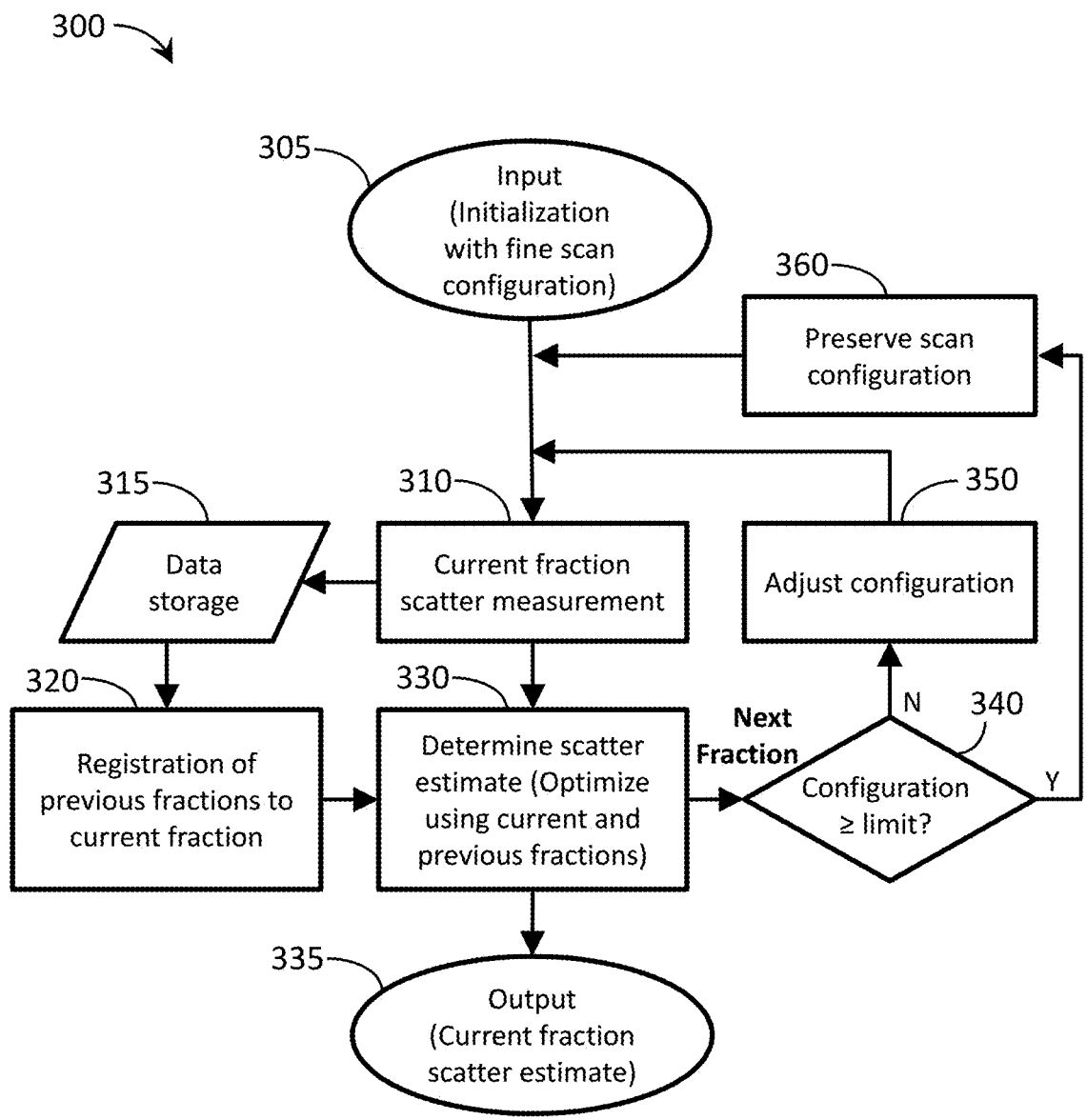
FIG. 3 is a flow chart depicting an exemplary method of scatter estimation using inter-fractional information.

FIG. 3 is a flow chart depicting an exemplary method 300 of scatter estimation using inter-fractional information. The method 300 can consider the entire treatment course as a whole and can utilize inter-fractional information to optimize the balance between scatter estimation, patient dose, and/or workflow. Generally, the method 300 can start with a fine scan configuration, such as, for example, a small helical pitch and a small beamformer opening for superior scatter estimation at the very beginning of the entire treatment course. Scatter for each fraction is estimated using the current measurement and those from previous fractions for improved estimation quality and/or stability. From fraction to fraction, the scan configuration can be loosened for improved workflow and reduced patient dose while maintaining adequate scatter estimation quality, including, for example, the same or improved scatter estimation quality.

The workflow can be continually adjusted (including, e.g., loosened to allow reduced quality scatter measurements or tightened to generate improved quality scatter measurements, associated with different scatter-to-primary ratios) as long as the configuration is within its limit(s), for example, at less than or equal to the maximum pitch allowed and/or at less than or equal to the maximum beamformer opening. The method 300 may be sufficient for a treatment course including a smaller number of fractions (without expected significant patient changes).

The method 300 can begin with input 305, including initialization with a fine scan configuration. Regarding the fine scan configuration, a scan protocol can be well designed (e.g., tight) in favor of scatter estimation, for example, with a small opening of the beamformer and a small pitch, so that the scatter estimation is very accurate for the first fraction. Although the time needed for this protocol may be relatively long, it can happen initially, for example, once or twice, and the impact can be considered acceptable for the entire treatment.

Step 310 includes scatter measurement for the current fraction The scatter measurement may be in conjunction with the overall measurement and processing of projection data (including primary data) from a radiation source directed towards a target, including, for example, using a rotating radiation source for emitting a radiation beam, a detector positioned to receive radiation from the radiation source, a beamformer with a beamformer opening configured to adjust a shape of the radiation beam emitted by the radiation source, and/or a data processing system, with scan configurations and parameter settings, as described above. Various scatter measurement methods may be applied, including, for example, using a beam stopper array or any of the other techniques described in the applications incorporated herein by reference, entitled "METHOD AND APPARATUS FOR SCATTER ESTIMATION IN CONE-BEAM COMPUTED TOMOGRAPHY" and, entitled "METHOD AND APPARATUS FOR IMPROVING SCATTER ESTIMATE AND CORRECTION IN X-RAY IMAGING.") Note that scatter measurement of all fractions can be stored at data storage 315, and will be available for subsequent fractions if there are any.

At step 320, data from the current fraction may be registered with one or more previous fractions. In various embodiments, this registration may be rigid or deformable, depending on practical considerations. These considerations can balance between speed, resources, and needs. While deformable registration may perform better, it can be more computationally expensive and may be more time consuming. Since the scatter is typically low frequency, a rigid registration may be sufficient for various applications. Therefore, both types of registration techniques are options and various embodiments are not limited to a specific one. Data storage 315 can also be used to store registered data and registration information, as well as any other data (e.g., as needed during current and/or subsequent fractions), associated with the disclosed techniques.

At step 330, the method can determine a scatter estimate for the current fraction based on the current fraction scatter measurement and at least one previous fraction scatter measurement. In one embodiment, this includes determining an intra-fraction scatter estimate based on the current fraction scatter measurement, determining an inter-fraction scatter estimate based on at least one previous fraction scatter measurement and a relationship between scatter and a scan parameter setting (e.g., where a current fraction scan configuration comprises at least one scan parameter setting different than a previous scan configuration), and determining the current fraction scatter estimate by combining the intra-fraction scatter estimate and the inter-fraction scatter estimate.

Step 330 can include optimization processes using data from both current and previous fractions. For example, an optimization process can be used for determining an improved estimation of scatter, primary, and/or a scatter-to-primary ratio (SPR). This optimization can consider both intra-fractional and inter-fractional (if available) information. For example, for the current fraction, step 330 can first estimate scatter, primary, and/or SPR information using intra-fractional information based on a selected technique. Then, assuming that there is an inherent relationship between fractions in terms of scatter information, the data can be improved or optimized.

Figure 7:
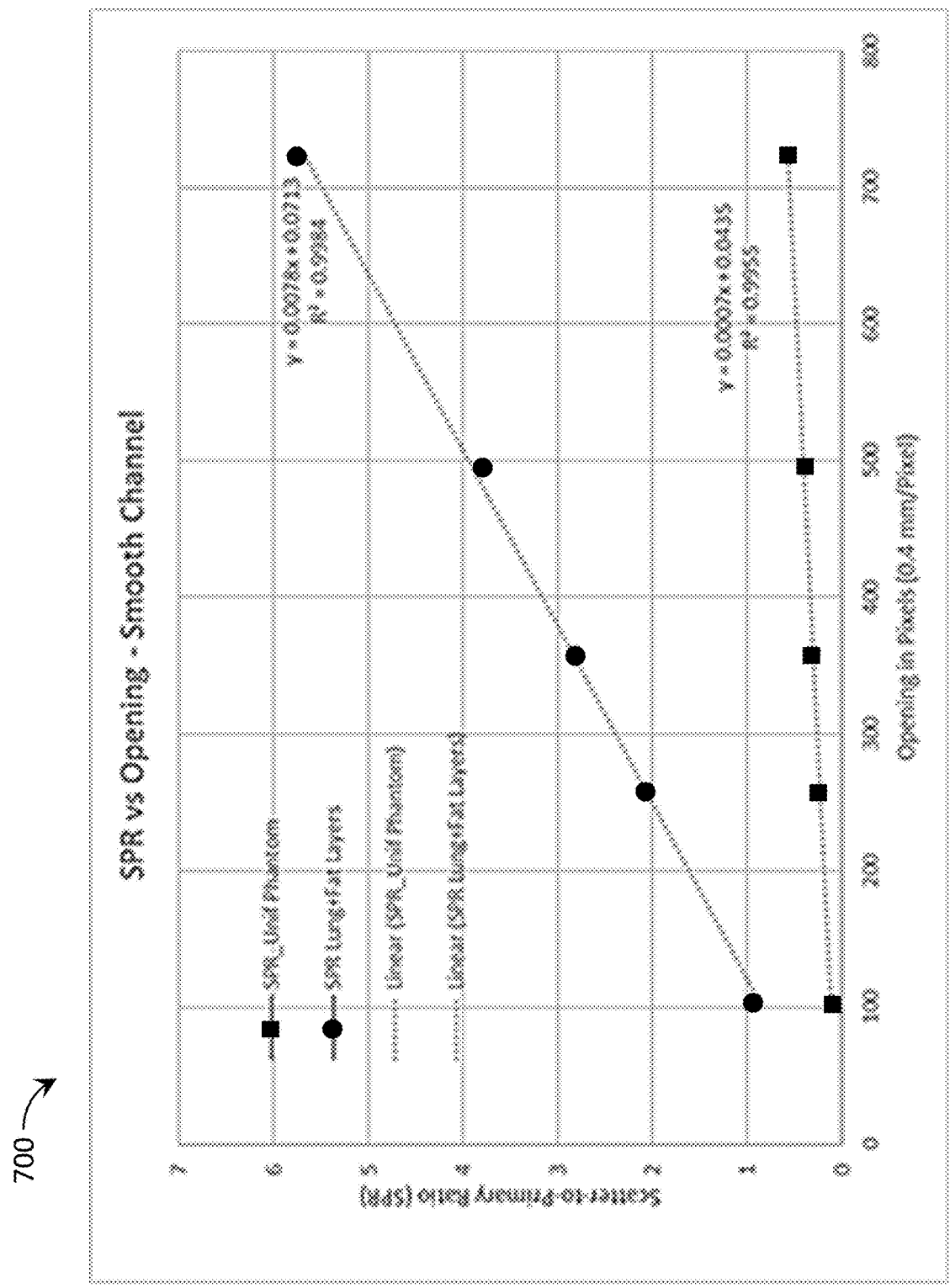
FIG. 7 is an illustration of an exemplary fitting process for SPR against the opening of the beamformer across different fractions.

For example, with additional reference to FIG. 7, assuming that the SPR is a function of the size of the beamformer opening scan parameter setting, the optimization can perform a fitting process for SPR against the opening of the beamformer across different fractions. FIG. 7 shows an exemplary linear relationship between beamformer opening and SPR for a phantom and lung plus fat layers. Various other relationships between scan parameter settings and scatter measurements can be used, including with use of non-linear fitting techniques. Such a process can also be used to exclude inaccurate scatter measurements that occurred due to, for example, an abrupt change of anatomy involved in views used for scatter estimation.

Next, in preparation for the next fraction, the method 300 determines if the scan configuration can be loosened, for example, to improve workflow or reduce patient dose, albeit by allowing a higher scatter-to-primary ratio. Configuration limits for scan parameters settings can be set to maintain a minimum level of scatter measurement quality during the loosening process. At step 340, the method determines if one or more configuration limits (e.g., associated with scan parameter settings) have been reached. In conjunction with improving workflow and reducing patient dose, a certain quality of scatter measurement (e.g., a maximum SPR) must be maintained. In various embodiments, scan parameter configuration limits can be set such that the associated scatter measurement meets a minimum image quality requirement depending on the needs of the application.

If one or more scan parameter settings have not yet reached their respective configuration limits, the method proceeds to step 350 and adjusts the scan configuration. This step is only performed if it is determined that further loosening of the scan configuration will not degrade the quality of the ultimate scatter estimation below a minimum level. Adjustments to scan parameter settings can be in accordance with any suitable algorithm or technique, including, for example, based on predetermined increments along linear or non-linear trajectories, percentages of remaining allowance before reaching configuration limit, combinations of parameter setting values (e.g., beamformer opening dependent on pitch/step size or vice versa), patient characteristics (e.g., BMI), combinations thereof, etc. In various embodiments, adjustments can be limited to apply to a small number of parameters, such as, for example, beamformer opening, patient support movement step size or effective pitch, etc. In various embodiments, adjustments can avoid changing other parameters, such as, for example, tube current, potential, filters, rotation time, etc.

In one embodiment, loosening a scan parameter setting for a subsequent fraction at step 350 is based on current fraction data and previous fraction data, where a subsequent fraction scatter measurement is associated with a higher SPR versus the current fraction scatter measurement because of the loosened scan parameter setting. In various embodiments, adjusting scan parameter settings for a subsequent fraction includes optimizing scatter estimation quality, workflow, and/or patient dose across different fractions in accordance with various priorities associated with the application/treatment. For example, the configuration limits and/or adjustments mentioned above can all be weighted differently to optimize or balance quality, time, and/or dose to different degrees in different situations.

If the available scan parameter settings have reached their respective configuration limits, the method proceeds to step 360 where the scan configuration for the next fraction is preserved or maintained without further loosening or degradation in quality.

The method then proceeds with the next fraction scatter measurement at step 310, continuing until the treatment is complete.

Figure 4:
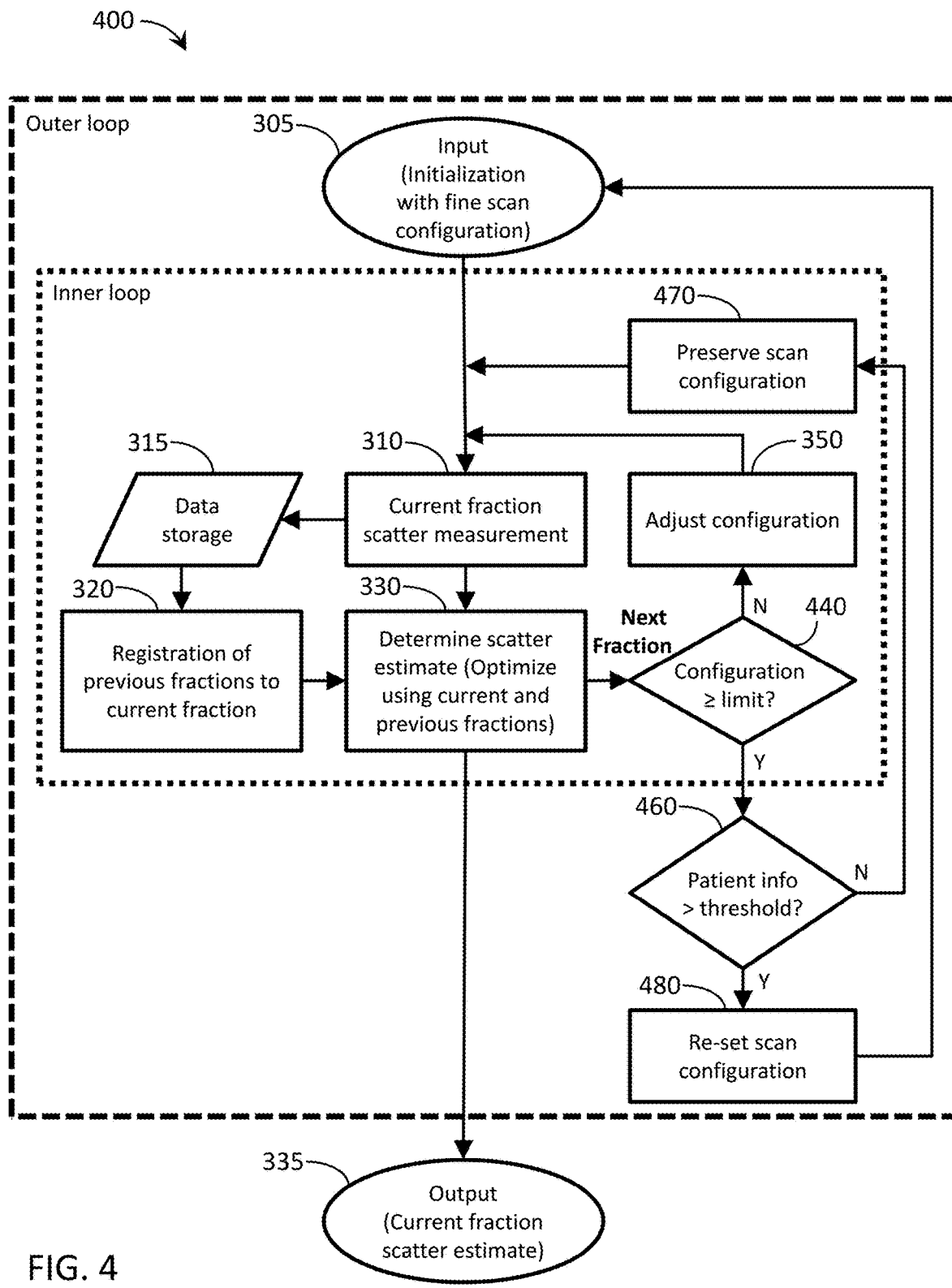
FIG. 4 is a flow chart depicting another exemplary method of scatter estimation using inter-fractional information.

FIG. 4 is a flow chart depicting another exemplary method 400 of scatter estimation using inter-fractional information. Like method 300, the method 400 can consider the entire treatment course as a whole and can utilize inter-fractional information to optimize the balance between scatter estimation, patient dose, and/or workflow. However, method 400 adds consideration of changes in the patient that may require a tightening or re-set of the scan configuration. For example, this may occur in situations where a patient change would reduce the applicability of prior fractions' scatter measurements to the current patient situation. (I.e., the assumptions discussed above for using prior fraction scatter measurements for a current fraction are based on a level of patient stability or consistency between fractions and become less applicable or reliable as the patient information changes.) This method 400 may be viewed as consisting of an inner loop adjusting the scan configuration similar to method 300 and an outer loop monitoring the patient information, for example, where the inner loop is a component of the outer loop.

Generally, the method 400 can start with a fine scan configuration, such as, for example, a small helical pitch and a small beamformer opening for superior scatter estimation at the very beginning of the entire treatment course. In the inner loop, as in method 300, scatter for each fraction is estimated using the current measurement and those from available previous fractions for improved estimation quality and stability. From fraction to fraction, the scan configuration can be adjusted (e.g., loosened) for improved workflow and reduced patient dose, while maintaining the same or improved scatter estimation quality. Like method 300, the workflow can be continually adjusted as long as the configuration is within its configuration limit(s) for various scan parameter settings. For example, at less than or equal to the maximum pitch allowed and/or at less than or equal to the maximum beamformer opening.

However, in method 400, the outer loop is designed to monitor patient information, including, for example, body mass index (BMI), to improve the stability of the method 400. If a substantial patient information or characteristic change is determined, for example, by comparing a measurable to a threshold, the scan configuration can be tightened or reset to a fine scan configuration before starting another inner loop.

For example, in one embodiment, the workflow may stay within the inner loop (e.g., as in method 300 described above) for a treatment course including a smaller number of fractions (without expected significant patient changes). In another embodiment, the outer loop may be utilized for a treatment course including a larger number of fractions depending on the amount of change occurring to the patient during the treatment course.

At step 440, in preparation for the next fraction as in step 340 of method 300 described above, the method 400 determines if the scan configuration can be loosened, for example, to improve workflow or reduce patient dose, albeit by allowing a higher scatter-to-primary ratio. If one or more scan parameter settings have not yet reached their respective configuration limits, the method proceeds to step 350 and adjusts the scan configuration.

However, if the available scan parameter settings have reached their respective configuration limits, method 400 proceeds to step 460 to check patient information. Patient information can be used to monitor the amount of change that has occurred in the patient, such as, for example, shape, weight, BMI, etc. Various thresholds can be defined so that if the amount of change of the monitored information exceeds a certain threshold (e.g., a 10% change in BMI), then the next fraction can include a scan configuration with tightened or reset scan parameter settings, resulting in a lower SPR. In various embodiments, determining if the patient information has exceeded the threshold can be based on one measurable, a plurality of measurables, and/or combinations of measurables, including where measurables have different weights and/or priorities.

If the patient information exceeds a threshold, the method proceeds to step 480 to reset the scan configuration by adjusting a scan parameter setting for a subsequent fraction such that the next fraction scatter measurement is improved versus the previous fraction scatter measurement because of the adjusted scan parameter setting. In this embodiment, re-setting the scan configuration includes starting the next fraction with a fine scan configuration at step 305, to re-estimate scatter with improved accuracy or quality. In various embodiments, the re-configuration can go back to that of the first fraction or can be adjusted (e.g., tightening) with a dedicated algorithm to improve the scatter measurement quality, depending on the application.

If the patient information does not exceed a threshold, the method proceeds to step 470 where the scan configuration for the next fraction is preserved or maintained without loosening or tightening to adjust the scatter measurement quality.

The method then proceeds with the next fraction scatter measurement at step 310, continuing until the treatment is complete.

It should be appreciated that the steps of determining if a scan parameter setting for the current fraction is less than a scan parameter limit and determining if a patient characteristic exceeds a characteristic threshold can be executed in different orders and at different times in various embodiments.

Figure 5:
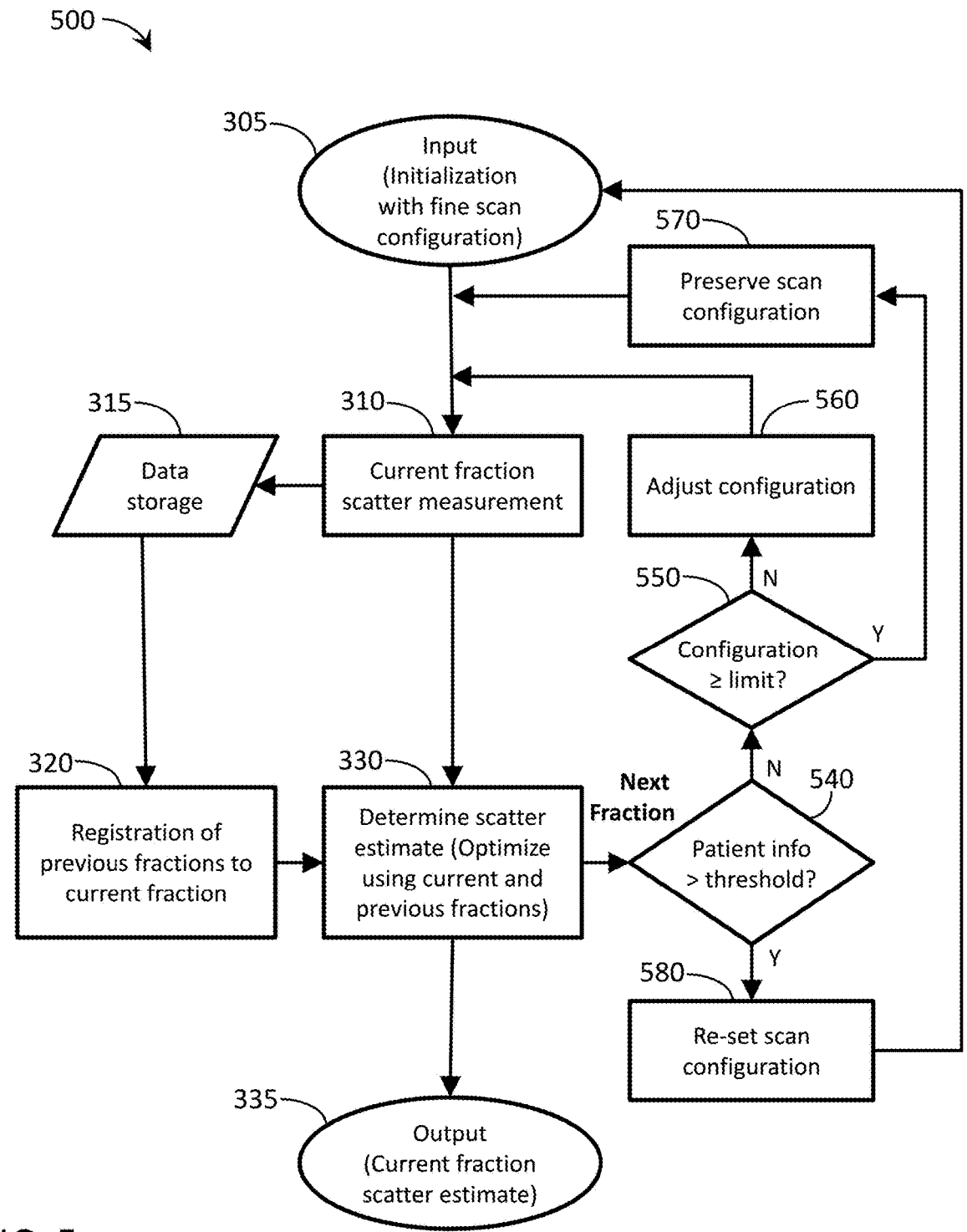
FIG. 5 is a flow chart depicting another exemplary method of scatter estimation using inter-fractional information.

For example, in one embodiment, FIG. 5 is a flow chart depicting another exemplary method 500 of scatter estimation using inter-fractional information. In this embodiment, step 540 determines if patient information has exceeded a threshold before the configuration limits are checked.

If the patient information does not exceed a threshold, the method 500 proceeds to step 550 to determine if the available scan parameter settings have reached their respective configuration limits. As discussed above, if the available scan parameter settings have not reached their respective configuration limits, the method proceeds to step 560 to adjust the scan configuration (e.g., loosening scan parameter settings). If the available scan parameter settings have reached their respective configuration limits, the method proceeds to step 570, preserving the current configuration.

If the patient information exceeds a threshold, the method 500 proceeds to step 580 to reset the scan configuration as discussed above. The other steps can be implemented similar to the steps of method 300.

Figure 6:
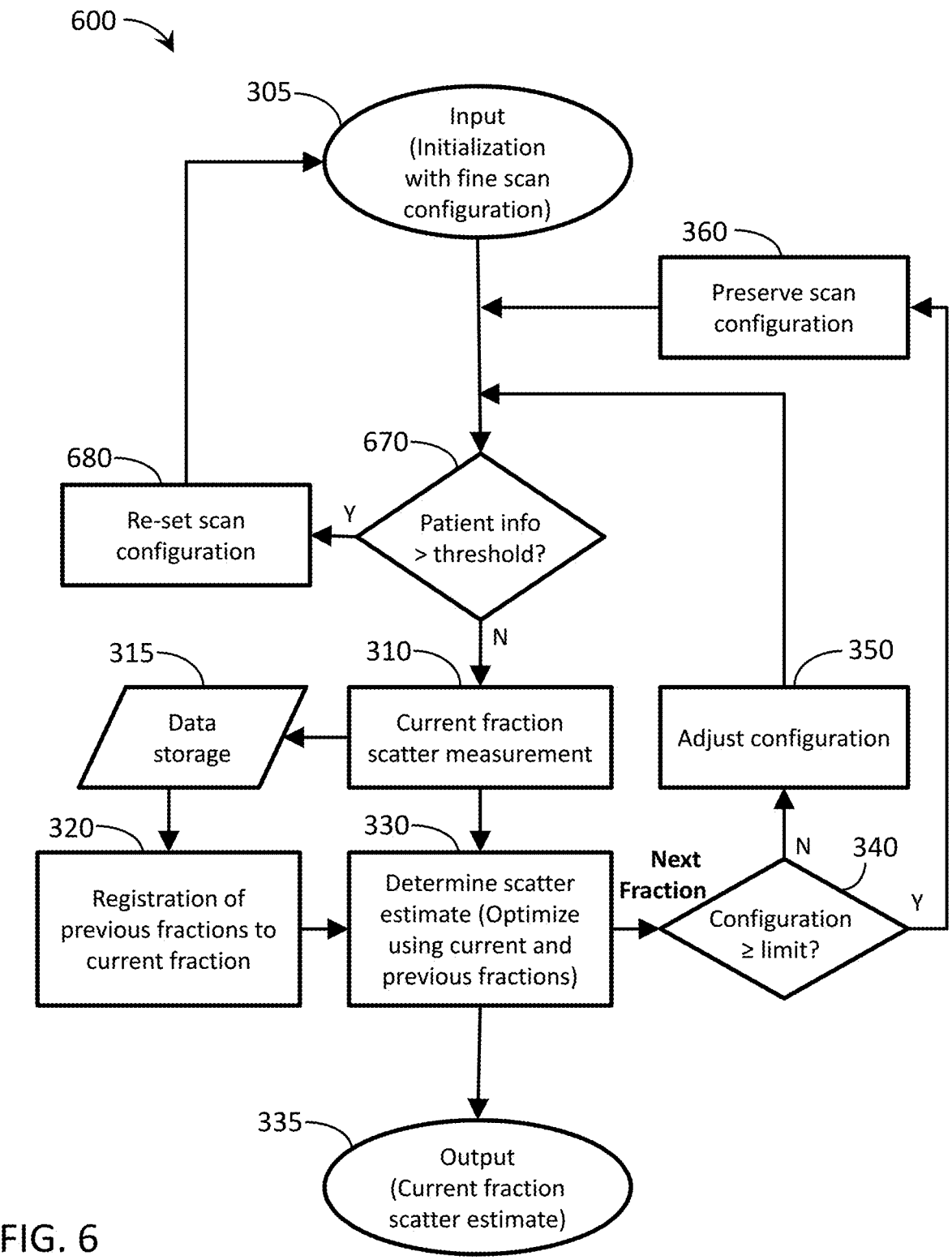
FIG. 6 is a flow chart depicting another exemplary method of scatter estimation using inter-fractional information.

In another embodiment, FIG. 6 is a flow chart depicting another exemplary method 600 of scatter estimation using inter-fractional information. In this embodiment, step 670 determines if patient information has exceeded a threshold before the current fraction scatter measurement at step 310.

If the patient information does not exceed a threshold, the method 600 proceeds to step 310 measure the current fraction scatter, as discussed above. If the patient information exceeds a threshold, the method 600 proceeds to step 680 to reset the scan configuration as discussed above. The remaining steps can be implemented similar to the steps of method 300.

FIG. 8 is a flow chart depicting an exemplary method 800 of scatter estimation and correction using inter-fractional data, such as those described above. Inputs can include any optional prior data and/or scan designs. In this embodiment, step 810 includes data acquisition. For example, during rotation of a radiation source projecting a collimated radiation beam towards a target and radiation detector, the method measures projection data (primary+scatter) during a current fraction, in accordance with any of the embodiments described above.

Data acquisition in step 810 can also include adjusting a shape/position of the radiation beam with the beamformer before and/or during the scan. Adjusting the radiation beam with the beamformer can include rotation and translation of highly attenuated material of the beamformer during the scan to change the shape/size of the radiation beam, including to generate more or less scatter during the scan.

Next, step 820 includes scatter estimation. For example, the method estimates the scatter in the projection data using scatter measurements from the current and previous fraction(s), in accordance with any of the embodiments described above. Then, step 830 includes scatter correction. For example, scatter estimated from step 820 is subtracted from the projection data to obtain scatter corrected projection data. Output includes scatter corrected projection data suitable for imaging. Various embodiments can utilize different scan geometries, detector positioning/active areas, beamformer positioning/window shapes, etc.

FIG. 9 is a flow chart depicting an exemplary method 900 of scatter estimation and correction using inter-fractional data, such as those described above. Inputs can include any optional prior data and/or scan designs. In this embodiment, step 910 includes data acquisition during fraction 1, which can be a previous fraction, where the method measures projection data (primary+scatter) during fraction 1. Next, at step 920, the method adjusts a scan parameter setting of the scan configuration based on the measured scatter, previous configuration settings, and/or patient information, as described above. For example, step 920 can adjust the beamformer opening and/or scan pitch/step size. Then, step 930 includes data acquisition during fraction 2, where the method measures projection data (primary+scatter) during fraction 2. Then, at step 940, the method can combine the measured scatter data from fraction 1 and fraction 2, including with use of various model fitting techniques.

Next, step 950 includes scatter estimation, where the method estimates the scatter in the projection data for fraction 2 using the scatter measurements from fraction 1 and fraction 2. Then, step 960 includes scatter correction, where the method subtracts the estimated scatter from the projection data to obtain scatter corrected projection data. Output includes scatter corrected projection data suitable for imaging. Like the steps of method 800, steps of method 900 can be implemented in accordance with any of the embodiments described above.

One or more optimization processes are also applicable to all of the above embodiments to determine scan parameters, adjustments, limits, thresholds, etc.

Figure 10:
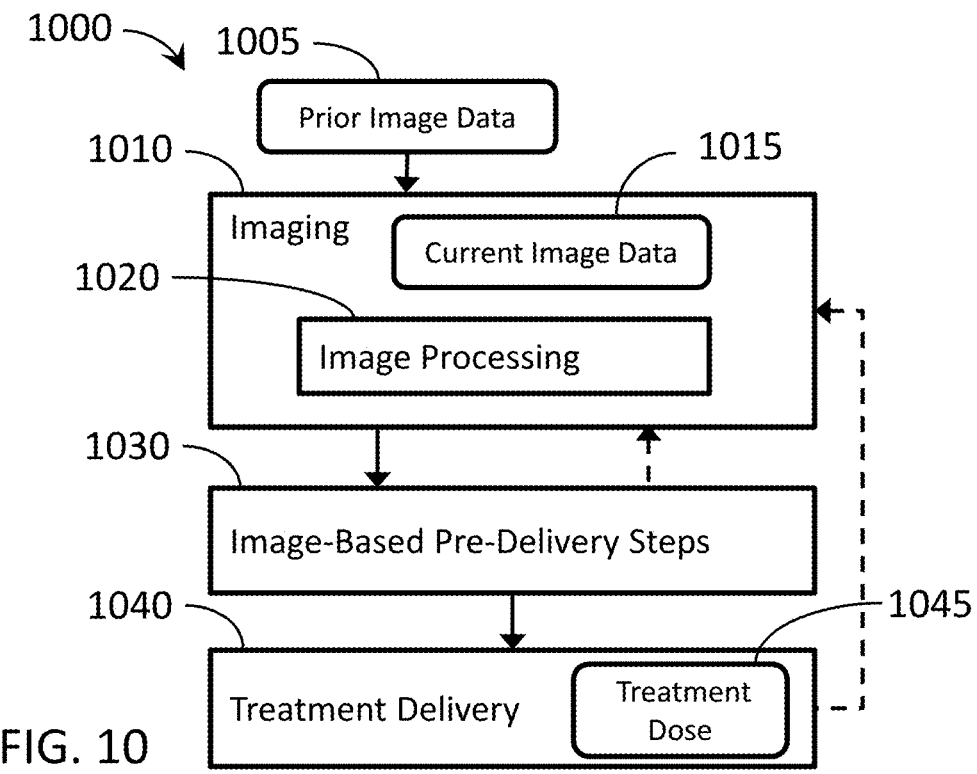
FIG. 10 is a flow chart depicting an exemplary method of IGRT using a radiotherapy device.

FIG. 10 is a flow chart depicting an exemplary method 1000 of IGRT using a radiotherapy device (including, e.g., x-ray imaging apparatus 10). Prior image data 1005 of the patient may be available for use, which may be a previously-acquired planning image, including a prior CT image. Prior data 1005 can also include treatment plans, phantom information, models, a priori information, etc. In some embodiments, prior image data 1005 is generated by the same radiotherapy device, but at an earlier time. Here, prior image data 1005 can also include data from previous fractions. At step 1010, imaging of a patient is performed using a source of low-energy radiation (e.g., kV radiation from x-ray source 30). In one embodiment, imaging comprises a helical scan(s) with a fan or cone beam geometry. Step 1010 can produce high-quality (HQ) image(s) or imaging data 1015 using the projection data processing techniques described above. In some embodiments, image quality may be adjusted to optimize a balance between image quality/resolution and dosage. In other words, not all images need to be of the highest quality or image quality may be adjusted to optimize or trade off a balance between image quality/resolution and image acquisition time. Imaging step 1010 can also include image processing to generate patient images based on the imaging data (e.g., in accordance with the methods described above). Although image processing step 1020 is shown as part of imaging step 1010, in some embodiments image processing step 1020 is a separate step, including where image processing is executed by separate devices.

Next, at step 1030, one or more image-based pre-delivery steps, discussed below, are performed based at least in part on the imaging data 1015 from step 1010. As discussed in more detail below, step 1030 can include determining various parameters associated with the therapeutic treatment and (subsequent) imaging planning. In some embodiments, image-based pre-delivery steps (1030) may require more imaging (1010) before treatment delivery (1040). Step 1030 can include adapting a treatment plan based on the imaging data 1015 as part of an adaptive radiotherapy routine. In some embodiments, image-based pre-delivery steps 1030 may include real-time treatment planning. Embodiments may also include simultaneous, overlapping, and/or alternating activation of the imaging and therapeutic radiation sources. Real-time treatment planning may involve any or all of these types of imaging and therapeutic radiation activation techniques (simultaneous, overlapping, and/or alternating).

Next, at step 1040, therapeutic treatment delivery is performed using a source of high-energy radiation (e.g., MV radiation from therapeutic radiation source 20). Step 1040 delivers a treatment dose 1045 to the patient according to the treatment plan. In some embodiments, the IGRT method 1000 may include returning to step 1010 for additional imaging at various intervals, followed by image-based pre-delivery steps (1030) and/or treatment delivery (1040) as required. In this manner the high-quality imaging data 1015 may be produced and utilized during IGRT using one apparatus 10 that is capable of adaptive therapy. As mentioned above, steps 1010, 1020, 1030, and/or 1040 may be executed simultaneously, overlapping, and/or alternating.

IGRT can include at least two general goals: (i) to deliver a highly conformal dose distribution to the target volume; and (ii) to deliver treatment beams with high accuracy throughout every treatment fraction. A third goal can be to accomplish the two general goals in as little time per fraction as possible. Delivering treatment beams accurately requires the ability to identify and/or track the location of the target volume intrafraction with high-quality images. The ability to increase delivery speed requires the ability to accurately, precisely, and quickly move the radiation source according to the treatment plan.

Figure 11:
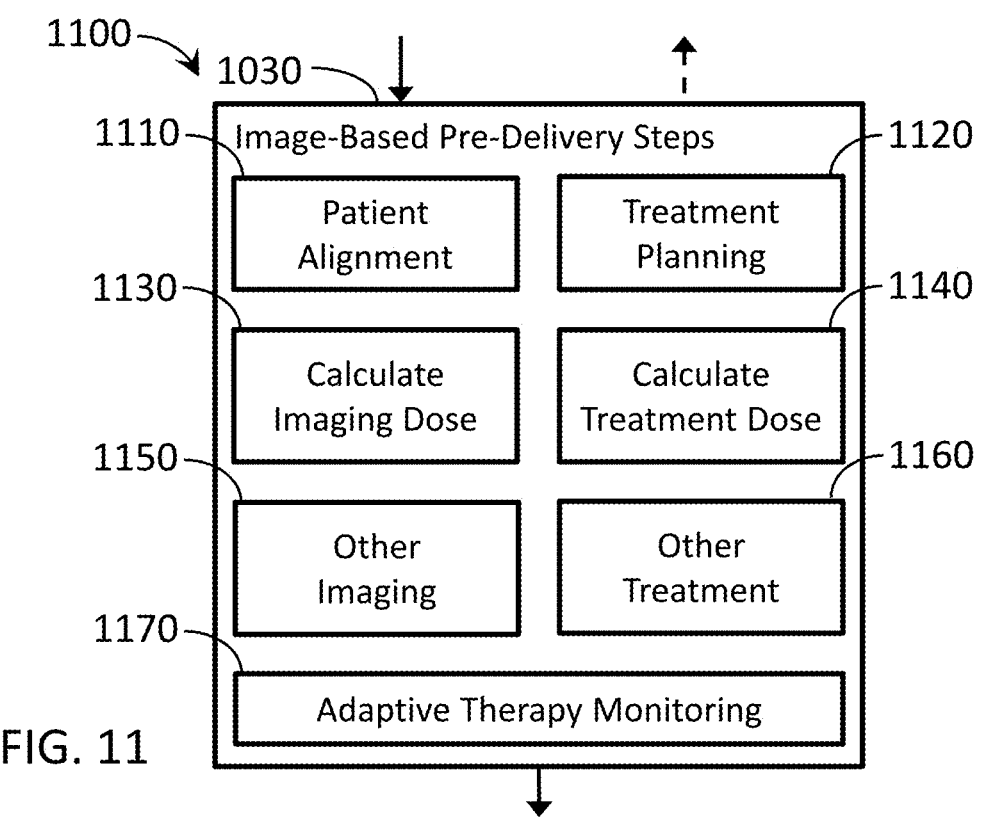
FIG. 11 is a block diagram depicting exemplary image-based pre-delivery steps.

FIG. 11 is a block diagram 1100 depicting exemplary image-based pre-delivery steps/options that may be associated with step 1030 above. It will be appreciated that the above-described x-ray imaging apparatus 10 (e.g., as part of a radiotherapy device) can generate kV images that can be used in a variety of ways, including for image-based pre-delivery steps (1030), without departing from the scope of the present invention. For example, images 1015 generated by the radiotherapy device can be used to align a patient prior to treatment (1110). Patient alignment can include correlating or registering the current imaging data 1015 with imaging data associated with earlier pre-treatment scans and/or plans, including the treatment plan. Patient alignment can also include feedback on the physical position of the patient relative to the radiation source to verify whether the patient is physically within the range of the delivery system. If necessary, the patient can be adjusted accordingly. In some embodiments, patient alignment imaging may purposely be of lesser quality to minimize dosage but provide adequate alignment information.

Images generated by the x-ray imaging apparatus 10 can also be used for treatment planning or re-planning (1120). In various embodiments, step 1120 can include confirming the treatment plan, modifying the treatment plan, generating a new treatment plan, and/or choosing a treatment plan from a set of treatment plans (sometimes referred to as "plan of the day"). For example, if the imaging data 1015 shows that the target volume or ROI is the same as when the treatment plan was developed, then the treatment plan can be confirmed. However, if the target volume or ROI is not the same, re-planning of the therapeutic treatment may be necessary. In the case of re-planning, because of the high quality of the imaging data 1015 (generated by the x-ray imaging apparatus 10 at step 1010), the imaging data 1015 may be used for treatment planning or re-planning (e.g., generating a new or modified treatment plan). In this manner, pre-treatment CT imaging via a different device is not necessary. In some embodiments, confirming and/or re-planning may be an ongoing procedure before and/or after various treatments.

In accordance with another exemplary use case, images generated by the x-ray imaging apparatus 10 can be used to calculate imaging dose (1130), which may be used for ongoing determinations of total dose to the patient and/or for subsequent imaging planning. The quality of subsequent imaging may also be determined as part of the treatment planning, for example, to balance quality and dosage. In accordance with another exemplary use case, images generated by the x-ray imaging apparatus 10 can be used to calculate treatment dose (1140), which may be used for ongoing determinations of total dose to the patient and/or may be included as part of treatment planning or re-planning.

In accordance with other exemplary use cases, images generated by the x-ray imaging apparatus 10 can be used in connection with planning or adjusting other imaging (1150) and/or other treatment (1160) parameters or plans, including, for example, as part of adaptive therapy and/or treatment plan generation. In accordance with another exemplary use case, images generated by the x-ray imaging apparatus 10 can be used in connection with adaptive therapy monitoring (1170), which can include monitoring treatment delivery and adapting as required.

It should be appreciated that the image-based pre-delivery steps (1030) are not mutually exclusive. For example, in various embodiments, calculate treatment dose (1140) can be a step by itself and/or can be part of adaptive therapy monitoring (1170) and/or treatment planning (1120). In various embodiments, the image-based pre-delivery steps (1030) can be performed automatically and/or manually with human involvement.

Figure 12:
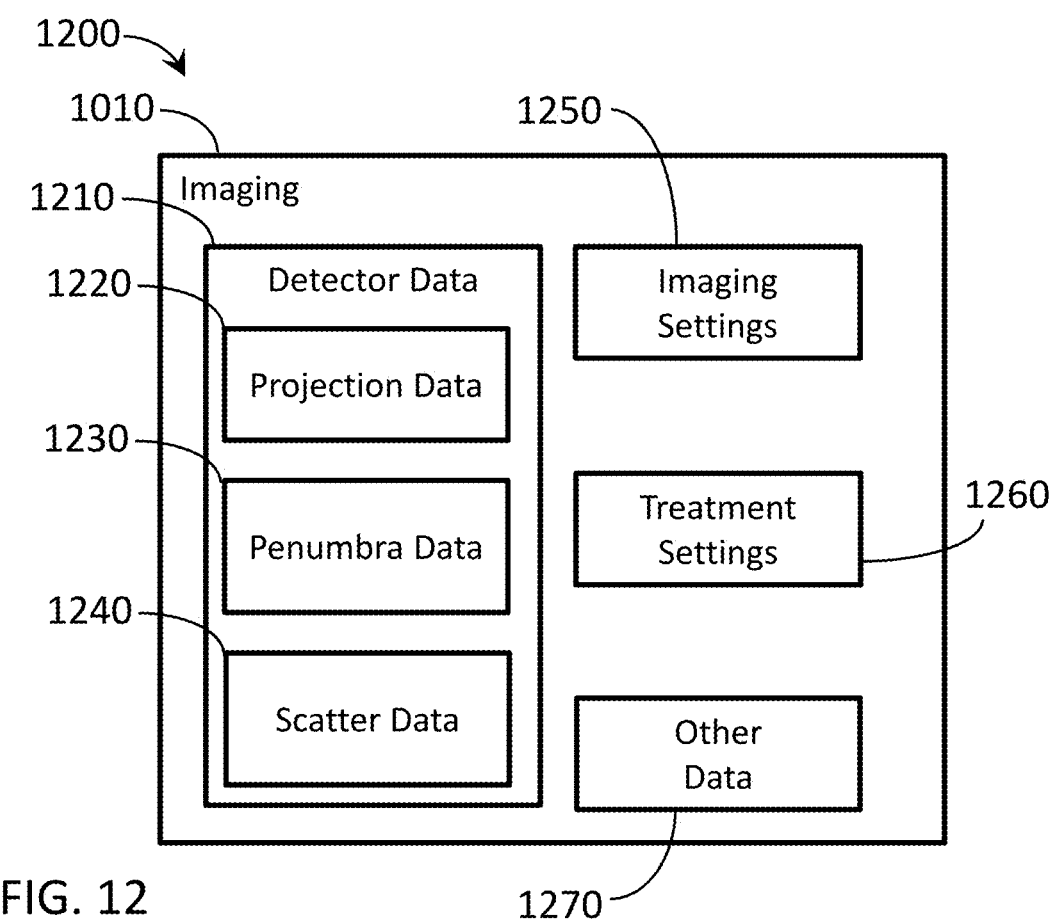
FIG. 12 is a block diagram depicting exemplary data sources that may be utilized during imaging or image-based pre-delivery steps.

FIG. 12 is a block diagram 1200 depicting exemplary data sources that may be utilized during imaging (1010) and/or subsequent image-based pre-delivery steps (1030). Detector data 1210 represents all of the data received by the image radiation detector 34. The projection data 1220 is the data generated by the radiation incident in the collimated beam area. The penumbra data 1230 is the data generated by the radiation incident in the penumbra area. The scatter data 1240 is the data generated by the radiation incident in the peripheral area outside of the penumbra area, which may be referred to as the shadow region(s). In some embodiments, scatter data can be generated separate from or in addition to the radiation incident in the shadow regions of the detector.

In one embodiment, the penumbra data 1230 may be used to separate or identify the projection and/or scatter data. In some embodiments, the scatter data 1240 can be used to estimate the scatter radiation in the projection data 1220. In another embodiment, the scatter data 1240 can be used to determine the residual effect of the scatter from the therapeutic radiation source 20 (e.g., MV) when the two sources 20, 30 are operated simultaneously or in an interleaved manner.

In this manner, the penumbra data 1230 and/or the scatter data 1240 may be utilized to improve the quality of the images generated by the imaging step 1010. In some embodiments, the penumbra data 1230 and/or the scatter data 1240 may be combined with the projection data 1220 and/or analyzed in view of the applicable imaging settings 1250, treatment settings 1260 (e.g., if simultaneous imaging and treatment radiation), and any other data 1270 associated with the x-ray imaging apparatus 10 at the time of the data collection at the imaging detector 34. In other embodiments, the data may be used for the treatment planning step 1030.

Although the disclosed technology has been shown and described with respect to a certain aspect, embodiment or embodiments, it is obvious that equivalent alterations and modifications will occur to others skilled in the art upon the reading and understanding of this specification and the annexed drawings. In particular regard to the various functions performed by the above described elements (components, assemblies, devices, members, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary aspect, embodiment or embodiments of the disclosed technology. In addition, while a particular feature of the disclosed technology may have been described above with respect to only one or more of several illustrated aspects or embodiments, such feature may be combined with one or more other features of the other embodiments, as may be desired and advantageous for any given or particular application.

While the embodiments discussed herein have been related to the systems and methods discussed above, these embodiments are intended to be exemplary and are not intended to limit the applicability of these embodiments to only those discussions set forth herein. While the present invention has been illustrated by the description of embodiments thereof, and while the embodiments have been described in some detail, it is not the intention of the applicant to restrict or in any way limit the scope of the appended claims to such detail. Additional advantages and modifications will readily appear to those skilled in the art. Therefore, the invention in its broader aspects is not limited to the specific details, representative apparatus and methods, and illustrative examples shown and described. Accordingly, departures may be made from such details without departing from the spirit or scope of the applicant's general inventive concept.

The invention claimed is:

1. An imaging apparatus for imaging across multiple fractions, comprising:
   a rotating radiation source for emitting a radiation beam;
   a detector positioned to receive radiation from the radiation source; a data processing system configured to:
   receive a previous fraction scatter measurement from a previous fraction;
   receive a current fraction scatter measurement from a current fraction, wherein a scatter-to-primary ratio during the current fraction is greater than during the previous fraction; and
   determine a current fraction scatter estimate based on the current fraction scatter measurement and the previous fraction scatter measurement.

2. The apparatus of claim 1, wherein a current fraction scan configuration comprises a scan parameter setting different than a previous scan configuration.

3. The apparatus of claim 2, wherein the scan parameter setting is based on a treatment plan and a patient characteristic.

4. The apparatus of claim 1, wherein a previous fraction scan configuration comprises scan parameter settings associated with a fine scan configuration.

5. The apparatus of claim 1, further comprising:
   a beamformer comprising a beamformer opening configured to adjust a shape of the radiation beam emitted by the radiation source;
   wherein the beamformer opening during the current fraction is larger than the beamformer opening during the previous fraction.

6. The apparatus of claim 1, wherein a pitch of a helical scan or a step size of a circular scan during the current fraction is larger than the pitch or the step size during the previous fraction.

7. The apparatus of claim 1, wherein the data processing system is further configured to:
   determine if a scan parameter setting for the current fraction is less than a scan parameter limit;
   if the scan parameter setting for the current fraction is less than the scan parameter limit, then adjusting the scan parameter setting for a subsequent fraction, wherein the scatter-to-primary ratio during the subsequent fraction is greater than during the current fraction based on the adjusted scan parameter setting; and
   if the scan parameter setting for the current fraction is not less than the scan parameter limit, then preserving the scan parameter setting for the subsequent fraction.

8. A method of estimating scatter during imaging across multiple fractions, comprising:
   receiving a previous fraction scatter measurement from a previous fraction;
   receiving a current fraction scatter measurement from a current fraction, wherein a scatter-to-primary ratio during the current fraction is greater than during the previous fraction;
   determining a current fraction scatter estimate based on the current fraction scatter measurement and the previous fraction scatter measurement; and
   reconstructing an image for the current fraction based on the current fraction scatter estimate.

9. The method of claim 8, wherein determining the current fraction scatter estimate comprises:
   determining an intra-fraction scatter estimate based on the current fraction scatter measurement;
   determining an inter-fraction scatter estimate based on at least one previous fraction scatter measurement and a relationship between scatter and a scan parameter setting, wherein a current fraction scan configuration comprises at least one scan parameter setting different than a previous scan configuration; and
   determining the current fraction scatter estimate based on the intra-fraction scatter estimate and the inter-fraction scatter estimate.

10. The method of claim 9, wherein the relationship between scatter and the scan parameter setting comprises the scatter-to-primary ratio based on a beamformer opening.

11. The method of claim 8, further comprising registering current fraction scan data with at least one previous fraction scan data.

12. The method of claim 8, further comprising adjusting at least one scan parameter setting for a subsequent fraction based on current fraction data and previous fraction data, wherein the scatter-to-primary ratio during the subsequent fraction is greater than during the current fraction based on the adjusted at least one scan parameter setting.

13. The method of claim 12, wherein adjusting at least one scan parameter setting for a subsequent fraction is further based on a patient characteristic.

14. The method of claim 12, wherein the at least one scan parameter setting comprises a pitch of a helical scan, a step size of a circular scan, or a beamformer opening size.

15. The method of claim 12, wherein adjusting the at least one scan parameter setting for a subsequent fraction comprises optimizing at least one of scatter estimation quality, workflow, or patient dose across different fractions.

16. The method of claim 8, further comprising:
determining if a scan parameter setting for the current fraction is less than a scan parameter limit;
if the scan parameter setting for the current fraction is less than the scan parameter limit, then adjusting the scan parameter setting for a subsequent fraction, wherein the scatter-to-primary ratio during the subsequent fraction is greater than during the current fraction based on the adjusted scan parameter setting; and
if the scan parameter setting for the current fraction is not less than the scan parameter limit, then preserving the scan parameter setting for the subsequent fraction.

17. The method of claim 8, further comprising:
determining if a patient characteristic exceeds a characteristic threshold; and
if the patient characteristic exceeds the characteristic threshold, then adjusting a scan parameter setting for a next fraction, wherein the scatter-to-primary ratio during the next fraction is less than during a previous fraction based on the adjusted scan parameter setting.

18. The method of claim 17, wherein adjusting the scan parameter setting comprises resetting the scan parameter setting to an initial setting associated with an initial scan configuration.

19. The method of claim 8, further comprising:
determining if a scan parameter setting for the current fraction is less than a scan parameter limit;
if the scan parameter setting for the current fraction is less than the scan parameter limit, then adjusting the scan parameter setting for a subsequent fraction, wherein the scatter-to-primary ratio during the subsequent fraction is greater than during the current fraction based on the adjusted scan parameter setting;
if the scan parameter setting for the current fraction is not less than the scan parameter limit, then determining if a patient characteristic exceeds a characteristic threshold; and
if the patient characteristic exceeds the characteristic threshold, then adjusting the scan parameter setting for the subsequent fraction, wherein the scatter-to-primary ratio during the subsequent fraction is less than during the current fraction based on the adjusted scan parameter setting.

20. A radiotherapy delivery device comprising:
a rotatable gantry system positioned at least partially around a patient support;
a first source of radiation coupled to the rotatable gantry system, the first source of radiation being configured as a source of therapeutic radiation;
a second source of radiation coupled to the rotatable gantry system, the second source of radiation being configured as a source of imaging radiation having an energy level less than the source of therapeutic radiation;
a radiation detector coupled to the rotatable gantry system and positioned to receive radiation from the second source of radiation; and
a data processing system configured to:
receive a previous fraction scatter measurement from a previous fraction;
receive a current fraction scatter measurement from a current fraction, wherein a scatter-to-primary ratio during the current fraction is greater than during the previous fraction; and
determine a current fraction scatter estimate based on the current fraction scatter measurement and the previous fraction scatter measurement;
reconstruct a patient image for the current fraction based on the current fraction scatter estimate; and
deliver a dose of therapeutic radiation to the patient via the first radiation source based on the patient image during adaptive IGRT.

\* \* \* \* \*